US011045109B2

(12) United States Patent
Tegg

(10) Patent No.: US 11,045,109 B2
(45) Date of Patent: Jun. 29, 2021

(54) NAVIGATIONAL ELECTRODE WITH MAGNETIC TRACKING COIL

(71) Applicant: St. Jude Medical International Holding S.à r.l., Luxembourg (LU)

(72) Inventor: Troy T. Tegg, Elk River, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 757 days.

(21) Appl. No.: 15/794,945

(22) Filed: Oct. 26, 2017

(65) Prior Publication Data
US 2018/0110440 A1 Apr. 26, 2018

Related U.S. Application Data

(60) Provisional application No. 62/413,075, filed on Oct. 26, 2016.

(51) Int. Cl.
| | | |
|---|---|---|
| *A61B 5/06* | (2006.01) | |
| *A61B 5/05* | (2021.01) | |
| *A61B 5/00* | (2006.01) | |
| *A61N 1/05* | (2006.01) | |
| *A61B 5/287* | (2021.01) | |

(52) U.S. Cl.
CPC ............. *A61B 5/062* (2013.01); *A61B 5/05* (2013.01); *A61B 5/06* (2013.01); *A61B 5/068* (2013.01); *A61B 5/287* (2021.01); *A61B 5/6885* (2013.01); *A61N 1/056* (2013.01); *A61N 1/0587* (2013.01)

(58) Field of Classification Search
CPC .. A61B 5/05; A61B 5/062; A61B 5/06; A61B 5/0422; A61B 5/068; A61N 1/056; A61N 1/0587
See application file for complete search history.

(56) References Cited

U.S. PATENT DOCUMENTS

| | | | |
|---|---|---|---|
| 6,233,476 B1 | 5/2001 | Strommer et al. | |
| 6,498,944 B1 | 12/2002 | Ben-Haim et al. | |
| 6,690,963 B2 | 2/2004 | Ben-Haim et al. | |
| 6,788,967 B2 | 9/2004 | Ben-Haim et al. | |
| 7,197,354 B2 | 3/2007 | Sobe | |
| 7,263,397 B2 | 8/2007 | Hauck et al. | |
| 7,386,339 B2 | 6/2008 | Strommer et al. | |
| 7,536,218 B2 | 5/2009 | Govari et al. | |
| 7,885,707 B2 | 3/2011 | Hauck | |
| 8,187,267 B2 | 5/2012 | Pappone et al. | |
| 8,567,265 B2 | 10/2013 | Aeby et al. | |
| 2007/0016007 A1* | 1/2007 | Govari ................. | A61B 5/0538 600/424 |
| 2008/0114230 A1* | 5/2008 | Addis .................... | A61N 1/056 600/373 |
| 2010/0152731 A1 | 6/2010 | de la Rama et al. | |

(Continued)

FOREIGN PATENT DOCUMENTS

WO 2016/149388 A1 9/2016

*Primary Examiner* — Amelie R Davis
(74) *Attorney, Agent, or Firm* — Dykema Gossett PLLC

(57) ABSTRACT

Embodiments of the present disclosure include a medical device, comprising an elongate shaft extending along a shaft longitudinal axis and comprising a shaft proximal portion and a shaft distal portion. A navigational assembly is connected to the shaft distal portion and extends along the shaft longitudinal axis. The navigational assembly includes a navigational electrode positioning feature and a magnetic position sensor positioning feature.

14 Claims, 17 Drawing Sheets

(56) References Cited

U.S. PATENT DOCUMENTS

| | | |
|---|---|---|
| 2011/0158488 A1 | 6/2011 | Cohen et al. |
| 2012/0010490 A1* | 1/2012 | Kauphusman .......... A61N 1/056 |
| | | 600/373 |
| 2012/0035466 A1* | 2/2012 | Tegg ...................... A61B 5/062 |
| | | 600/424 |
| 2012/0169712 A1* | 7/2012 | Hill ........................ G06T 15/08 |
| | | 345/419 |
| 2014/0200441 A1 | 7/2014 | Potter et al. |
| 2015/0351832 A1 | 12/2015 | Oliverius et al. |
| 2016/0235338 A1* | 8/2016 | Sekiguchi .......... A61B 1/00043 |

* cited by examiner

278

```
┌─────────────────────────────────────────────────────┐
│ GENERATING AN ELECTRICAL FIELD WITH A CURRENT SOURCE│──280
│ AND A MAGNETIC FIELD WITH A MAGNETIC FIELD GENERATOR│
└─────────────────────────────────────────────────────┘
                          │
┌─────────────────────────────────────────────────────┐
│ RECEIVING AN ELECTRODE POSITION SIGNAL FROM AN      │
│ ELECTRODE POSITIONED ON THE MEDICAL DEVICE, THE     │──282
│ ELECTRODE POSITION SIGNAL BEING GENERATED AS A RESULT│
│ OF THE ELECTRODE BEING EXPOSED TO THE ELECTRICAL FIELD│
└─────────────────────────────────────────────────────┘
                          │
┌─────────────────────────────────────────────────────┐
│ RECEIVING A MAGNETIC POSITION SIGNAL FROM A MAGNETIC│
│ POSITION SENSOR POSITIONED ON THE MEDICAL DEVICE, THE│
│ MAGNETIC POSITION SIGNAL BEING GENERATED AS A RESULT OF│──284
│ THE MAGNETIC POSITION SENSOR BEING EXPOSED TO THE   │
│ MAGNETIC FIELD                                      │
└─────────────────────────────────────────────────────┘
                          │
┌─────────────────────────────────────────────────────┐
│ DETERMINING A MAGNETIC POSITION BASED ON THE MAGNETIC│
│ POSITION SIGNAL AND AN ELECTRODE POSITION BASED ON THE│──286
│ ELECTRODE POSITION SIGNAL                           │
└─────────────────────────────────────────────────────┘
                          │
┌─────────────────────────────────────────────────────┐
│ DETERMINING A ROTATION OF THE MEDICAL DEVICE BASED ON A│
│ SHIFT IN THE ELECTRODE POSITION WITH RESPECT TO THE │──288
│ MAGNETIC POSITION                                   │
└─────────────────────────────────────────────────────┘
```

*FIG. 8*

NAVIGATIONAL ELECTRODE WITH MAGNETIC TRACKING COIL

CROSS-REFERENCE TO RELATED APPLICATIONS

This application claims priority to U.S. provisional patent application No. 62/413,075 titled "NAVIGATIONAL ELECTRODE WITH MAGNETIC TRACKING COIL," filed 26 Oct. 2016, which is hereby incorporated by reference as though fully set forth herein.

BACKGROUND a. Field

The present disclosure relates generally to navigational electrode with magnetic tracking coil.

b. Background

Medical devices such as guidewires, catheters, introducers and the like that include electromagnetic coil position sensors or electrodes for device navigation are used in various medical procedures in the body. For example, it is known to equip a catheter with multiple coils sufficient to allow a position sensing system to detect six (6) degrees-of-freedom (DOF), namely, a three-dimensional (3D) position (X, Y, Z) and a 3D orientation (e.g., roll, pitch, yaw) thereof. However, the design of a coil assembly that can provide such functionality provides challenges, particularly with respect to space constraints.

SUMMARY

Embodiments of the present disclosure include a medical device, comprising an elongate shaft extending along a shaft longitudinal axis and comprising a shaft proximal portion and a shaft distal portion. A navigational assembly is connected to the shaft distal portion and extends along the shaft longitudinal axis. The navigational assembly includes a navigational electrode positioning feature and a magnetic position sensor positioning feature.

Embodiments of the present disclosure include a medical device, comprising an elongate shaft extending along a shaft longitudinal axis and comprising a shaft proximal end and a shaft distal end. A central mounting bore including a bore proximal end and a bore distal end, can be connected to the shaft distal end. A navigational assembly can define an elongate central lumen through which the central mounting bore passes. The navigational assembly can include a recessed pocket in which a navigational electrode is disposed. A tip assembly can be connected to the distal end of the central mounting bore.

Embodiments of the present disclosure include a method for determining a position and orientation of a medical device. In some embodiments, the method can include generating an electrical field with a current source and a magnetic field with a magnetic field generator. In some embodiments, the method can include receiving an electrode position signal from an electrode positioned on the medical device, the electrode position signal being generated as a result of the electrode being exposed to the electrical field. In some embodiments, the method can include receiving a magnetic position signal from a magnetic position sensor positioned on the medical device, the magnetic position signal being generated as a result of the magnetic position sensor being exposed to the magnetic field. In some embodiments, the method can include determining a magnetic position based on the magnetic position signal and an electrode position based on the electrode position signal. In some embodiments, the method can include determining a rotation of the medical device based on a shift in the electrode position with respect to the magnetic position.

BRIEF DESCRIPTION OF THE DRAWINGS

FIG. 8 is a method flow diagram for determining a position and orientation of a medical device, in accordance with embodiments of the present disclosure.

DETAILED DESCRIPTION

Figure 1:
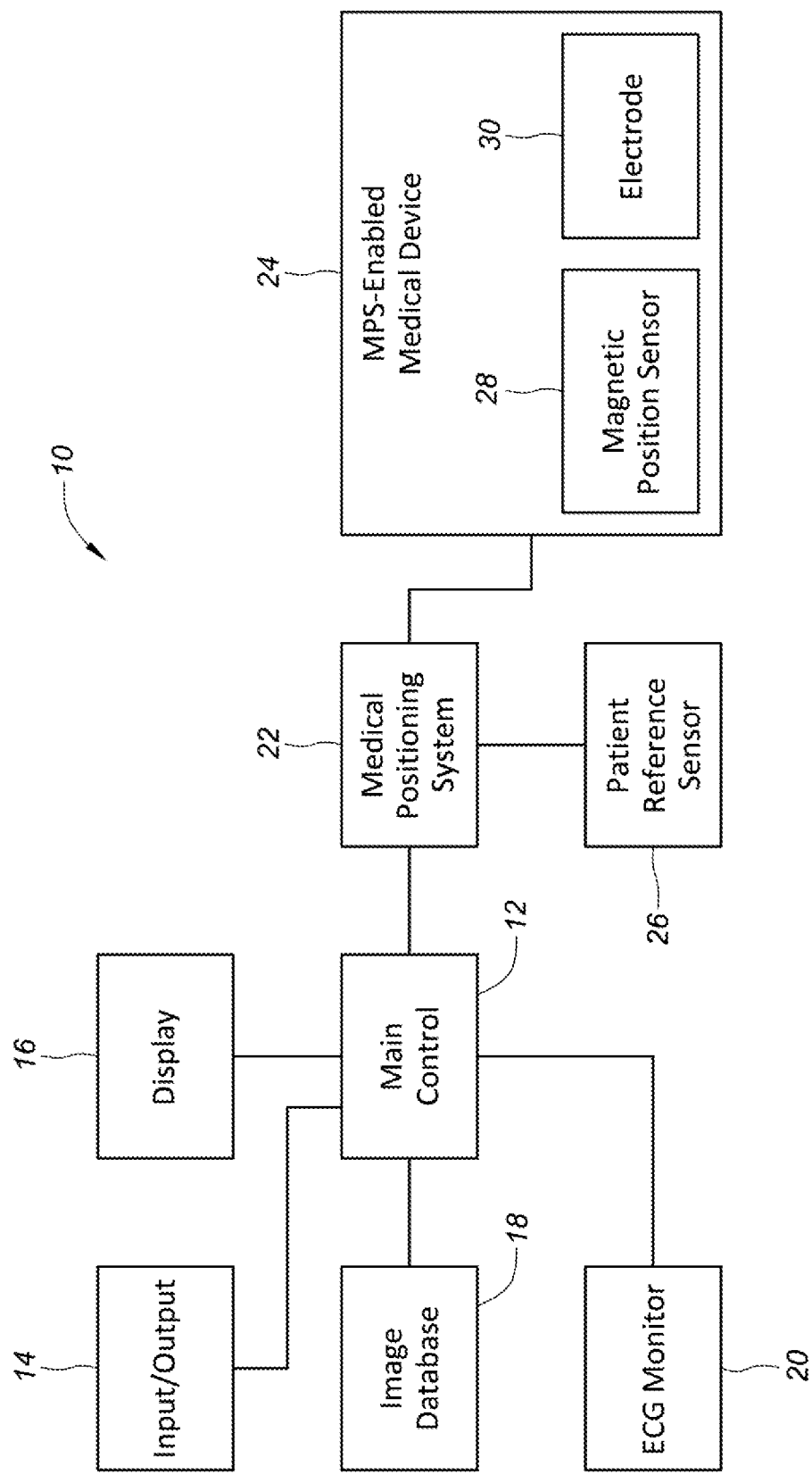
FIG. 1 depicts a schematic and block diagram view of an electromagnetic navigation system, in accordance with embodiments of the present disclosure.

FIG. 1 is a diagrammatic view of a system 10 in which a medical device, such as a guidewire, catheter, introducer (e.g., sheath) incorporating a magnetic position sensor 28 and an electrode 30 may be used. Before proceeding to a detailed description of the embodiments of the present disclosure, a description of an exemplary environment in which such devices and sensors may be used will first be set forth. With continued reference to FIG. 1, system 10, as depicted, includes a main electronic control unit 12 (e.g., a processor) having various input/output mechanisms 14, a display 16, an optional image database 18, an electrocardiogram (ECG) monitor 20, a localization system, such as a medical positioning system 22, a medical positioning system-enabled elongate medical device 24, a patient reference sensor 26, a magnetic position sensor 28 and an electrode 30. For simplicity, one magnetic position sensor 28 and one electrode 30 are shown, however, more than one magnetic position sensor 28 and/or more than one electrode 30 can be included in the system 10.

Input/output mechanisms 14 may comprise conventional apparatus for interfacing with a computer-based control unit including, for example, one or more of a keyboard, a mouse, a tablet, a foot pedal, a switch and/or the like. Display 16 may also comprise conventional apparatus, such as a computer monitor.

Various embodiments described herein may find use in navigation applications that use real-time and/or pre-acquired images of a region of interest. Therefore, system 10 may optionally include image database 18 to store image information relating to the patient's body. Image information may include, for example, a region of interest surrounding a destination site for medical device 24 and/or multiple regions of interest along a navigation path contemplated to be traversed by medical device 24. The data in image database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus), wherein the image database acts as a buffer (live fluoroscopy); and/or (3) a sequence of related two-dimensional images defining a cine-loop wherein each image in the sequence has at least an ECG timing parameter associated therewith, adequate to allow playback of the sequence in accordance with acquired real-time ECG signals obtained from ECG monitor 20. It should be understood that the foregoing embodiments are examples only and not limiting in nature. For example, the image database may also include three-dimensional image data as well. It should be further understood that the images may be acquired through any imaging modality, now known or hereafter developed, for example X-ray, ultra-sound, computerized tomography, nuclear magnetic resonance or the like.

ECG monitor 20 is configured to continuously detect an electrical timing signal of the heart organ through the use of a plurality of ECG electrodes (not shown), which may be externally-affixed to the outside of a patient's body. The timing signal generally corresponds to a particular phase of the cardiac cycle, among other things. Generally, the ECG signal(s) may be used by the control unit 12 for ECG synchronized play-back of a previously captured sequence of images (cine loop) stored in database 18. ECG monitor 20 and ECG-electrodes may both comprise conventional components.

Medical positioning system 22 is configured to serve as the localization system and therefore to determine position (localization) data with respect to one or more magnetic position sensors 28 and/or electrodes 30 and output a respective location reading. The location readings may each include at least one or both of a position and an orientation (P&O) relative to a reference coordinate system (e.g., magnetic based coordinate system, impedance based coordinate system), which may be the coordinate system of medical positioning system 22. For some types of sensors, the P&O may be expressed with five degrees-of-freedom (five DOF) as a three-dimensional (3D) position (e.g., a coordinate in three perpendicular axes X, Y and Z) and two-dimensional (2D) orientation (e.g., a pitch and yaw) of an electromagnetic position sensor 28 in a magnetic field relative to a magnetic field generator(s) or transmitter(s) and/or electrode 30 in an applied electrical field relative to an electrical field generator (e.g., a set of electrode patches). For other sensor types, the P&O may be expressed with six degrees-of-freedom (six DOF) as a 3D position (e.g., X, Y, Z coordinates) and 3D orientation (e.g., roll, pitch, and yaw).

One known electromagnetic position sensor includes a coil wound symmetrically on a tubular core. Such a sensor may be seen by reference to U.S. Pat. No. 7,197,354, entitled "System for Determining the Position and Orientation of a Catheter" issued to Sobe, hereby incorporated by reference in its entirety as though fully set forth herein. Sobe discloses a core that is hollow, is symmetric about a central axis, and can be scaled in length, inner diameter, and outer diameter for a particular application. A coil is wound on the core in a desired winding pattern. The coil, like the core, is symmetric about the central axis. The sensor can be used in a system to detect position in 3D space defined by three perpendicular axes (X, Y, and Z), as well as rotation about two of the three axes (e.g., pitch and yaw), but the coil cannot detect rotation about the central axis of the core (e.g., roll). Accordingly, a medical device that incorporates a single sensor coil mounted symmetric about the central axis of the medical device only senses five (5) DOF, that is, two orientation parameters, in addition to three position parameters. Despite the DOF limitation, there are nonetheless desirable aspects of the above configuration. For example, the configuration uses minimal space and accommodates an open central lumen.

Electrode mapping systems, particularly the EnSite™ Velocity™ cardiac mapping system available from St. Jude Medical, or as seen generally, for example, by reference to U.S. Pat. No. 7,263,397, or U.S. Pat. No. 7,885,707, both of which are hereby incorporated by reference as though fully set forth herein, utilize an electrical field to localize a medical device within a patient's body. As is known, electrodes can be disposed in a spaced apart relationship along an axis of a catheter shaft. The electrodes can detect the electrical field generated by such a system and thereby detect position in 3D space defined by three perpendicular axes (X, Y, and Z), as well as rotation about two of the three axes (e.g., pitch and yaw), but the electrodes cannot detect rotation about the central axis of the catheter shaft (e.g., roll).

Medical positioning system 22 determines respective locations (e.g., P&O) in the reference coordinate system based on capturing and processing signals received from the magnetic position sensor 28 while the sensor is disposed in a controlled low-strength alternating current (AC) magnetic (e.g., magnetic) field and signals received from the electrode 30 while the electrodes are disposed in a controlled electrical field generated by electrode patches, for example. Further aspects of a visualization, navigation, and/or mapping system that can be employed with embodiments of the present disclosure are discussed with respect to FIGS. 12 and 13.

Each magnetic position sensor 28 and the like may comprise a coil and, from an electromagnetic perspective, the changing or AC magnetic field may induce a current in the coil(s) when the coil(s) are in the magnetic field. The magnetic position sensor 28 is thus configured to detect one or more characteristics (e.g., flux) of the magnetic field(s) in which it is disposed and generate a signal indicative of those characteristics, which is further processed by medical positioning system 22 to obtain a respective P&O for the magnetic sensor 28. The electrode 30 may comprise a ring electrode, in some examples. The electrode 30 can be configured to detect one or more characteristics (e.g., current) of the electrical field(s) in which it is disposed and generate a signal indicative of those characteristics, which is further processed by medical positioning system 22 to obtain a respective P&O for the plurality of electrode 30.

Referring still to FIG. 1, in an embodiment, medical positioning system 22 may determine the P&O of medical positioning system enabled medical device 24 according to certain physical characteristics of electromagnetic position sensor 28 and electrode 30 in addition to the signals received from magnetic position sensor 28 and electrode 30. Such characteristics may include predetermined calibration data, for example, indicative of or corresponding to the respective winding angles of one or more portions of a coil on sensor 28, the number of coil portions, the type(s) of conductor used in the coil, and the direction and number of loops in the coil. In addition, such characteristics may include predetermined calibration data, for example, indicative of or corresponding to a position of electrode 30, the number of electrodes 30, size of electrode 30, shape of electrode 30, and type of material(s) the electrodes are formed of. Medical positioning system 22 may have such characteristics of the magnetic position sensor 28 and/or electrode 30 pre-programmed, may determine such characteristics from a calibration procedure, or may receive such characteristics from a storage element coupled with medical device 24.

Magnetic position sensor 28 and the electrode 30 may be associated with medical positioning system enabled medical device 24. Another medical positioning system sensor, namely, patient reference sensor (PRS) 26 (if provided in system 10) can be configured to provide a positional reference of the patient's body so as to allow motion compensation for patient body movements, such as respiration-induced movements. Such motion compensation is described in greater detail in U.S. patent application Ser. No. 12/650,932, entitled "Compensation of Motion in a Moving Organ Using an Internal Position Reference Sensor", hereby incorporated by reference in its entirety as though fully set forth herein. PRS 26 may be attached to the patient's manubrium sternum or other location. Like the magnetic position sensor 28, PRS 26 can be configured to detect one or more characteristics of the magnetic field in which it is disposed, wherein medical positioning system 22 determines a location reading (e.g., a P&O reading) indicative of the PRS's position and orientation in the reference coordinate system. In some embodiments, an additional PRS can be configured to detect one or more characteristics of the electrical field in which it is disposed, wherein the medical positioning system 22 determines a location reading (e.g., a P&O reading) indicative of the PRS's position and orientation in the reference coordinate system.

FIG. 2 is an isometric side, bottom, and rear view of a medical device 110 that includes a navigational assembly 140 and a flexible tip assembly 130 disposed at a distal end of an elongate shaft 112, in accordance with embodiments of the present disclosure. In some embodiments, the elongate shaft 112 can be a deflectable shaft and can extend along a shaft longitudinal axis and can comprise a shaft proximal portion and a shaft distal portion. For example, the elongate shaft 112 can be formed of a material that provides for a deflection of the elongate shaft 112. The elongate shaft 112 can be sized and configured to be inserted into the human body, and can be deflectable to enable the elongate shaft 112 to be guided through a tortuous vasculature of a patient. The position of the shaft can be determined through one or more ring electrodes 114-1, 114-2 disposed along the elongate shaft 112. In some embodiments, the ring electrodes 114-1, 114-2 can generate signals in response to being disposed in an applied electrical field, which can be analyzed to determine a position and/or orientation of the medical device 110. In some embodiments, the ring electrodes can be used to collect electrical signals produced by tissue for diagnostic purposes.

Figures 2A, 2B:
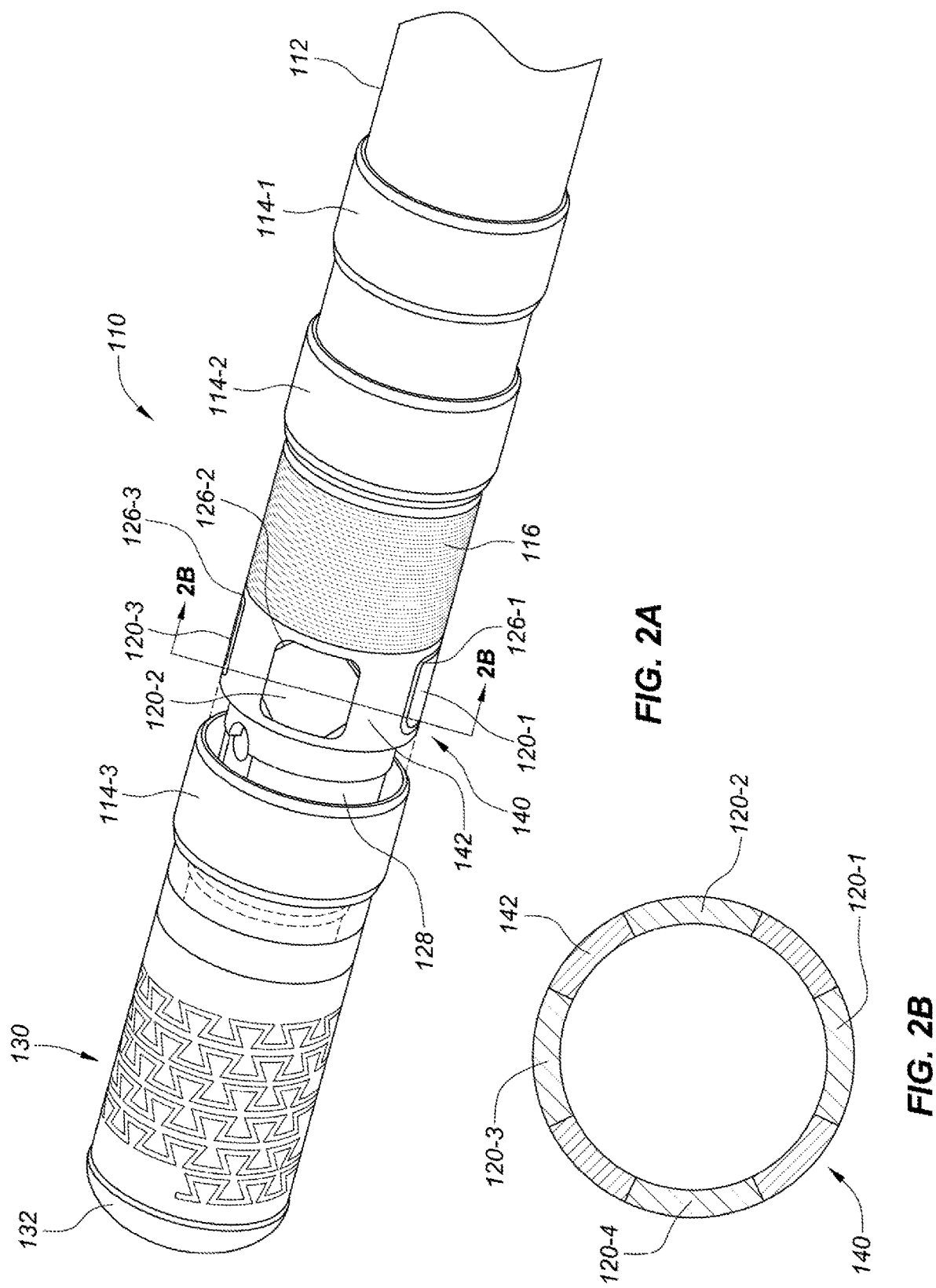
FIG. 2A is an isometric side, bottom, and rear view of a medical device that includes a navigational assembly and a flexible tip assembly disposed at a distal end of an elongate shaft, in accordance with embodiments of the present disclosure.
FIG. 2B is a cross-sectional view of the navigational assembly depicted in FIG. 2A, in accordance with embodiments of the present disclosure.

In some embodiments, the medical device 110 can include a navigational assembly 140, which can be disposed on the shaft distal portion and can extend along the shaft longitudinal axis. The navigational assembly 140 can include a navigational assembly base 142, which is further discussed in relation to FIG. 4. The navigational assembly base 142 can be formed from a non-conductive material (e.g., nylon, polyether block amide (Pebax®), ceramic, etc.) and can be configured to house navigational electrodes 120-1, 120-2, 120-3, 120-4 (FIG. 2B), hereinafter generally referred to in the plural as navigational electrodes 120, and a magnetic position sensor 116, in accordance with embodiments of the present disclosure. In at least one embodiment, the navigational electrodes 120 may comprise spot electrodes, that is they do not span the entire circumference of medical device 110, as do ring electrodes 114 and rather are positioned at relatively well defined and constrained locations or spots about the device's circumference. Although only three navigational electrodes 120-1, 120-2, 120-3 are depicted in FIG. 2A, an additional navigational electrode 120-4 is hidden from view and is depicted in FIG. 2B, which is a cross-sectional view of the navigational assembly along line 2B-2B in FIG. 2A. For example, a fourth navigational electrode 120-4 can be diametrically opposed from the second navigational electrode 120-2.

In some embodiments, although four navigational electrodes 120 are discussed in relation to the navigational assembly 140, the navigational assembly 140 can include fewer than four navigational electrodes 120 or greater than four navigational electrodes 120 in some embodiments. In some embodiments, regardless of the number of the navigational electrodes disposed on the navigational assembly 140, the navigational electrodes 120 can be equally spaced about the circumference of the navigational assembly 140. For example, as depicted in FIGS. 2A and 2B, where four navigational electrodes 120 are disposed on the navigational assembly 140, the navigational electrodes 120 can be spaced approximately 90 degrees apart from one another. In an example where there are three navigational electrodes 120 disposed on the navigational assembly 140, the navigational electrodes 120 can be spaced approximately 120 degrees apart from one another. In an example where there are six navigational 120 disposed on the navigational assembly 140, the navigational electrodes 120 can be spaced approximately 60 degrees apart from one another. Although the navigational electrodes 120 are discussed herein as being used for navigational purposes, the navigational electrodes 120 can also be used for collecting electrical signals produced by tissue for diagnostic purposes. Additionally, the navigational electrodes 120 can be configured to deliver therapeutic energy in a unipolar and/or bipolar mode. In some embodiments, the navigational electrodes 120 can be configured to deliver therapeutic energy in conjunction with the flexible tip assembly 130, spot electrode, ring electrode 114-1, 114-2, etc.

In some embodiments, the navigational assembly 140 can include a magnetic position sensor 116 disposed on the navigational assembly base 142. As previously discussed, the magnetic position sensor 116 can produce a signal in response to being positioned in a magnetic field. The signal can be analyzed to determine a position and/or orientation of the medical device 10. As depicted, the magnetic position sensor 116 can be a coil formed by winding a filament around an elongate axis. As depicted, the magnetic position sensor 116 is wound around an outer surface of the navigational assembly base 142.

In some embodiments, the navigational assembly base 142 can include navigational electrode positioning features 126-1, 126-2, 126-3, hereinafter generally referred to in the plural as navigational electrode positioning features 126. The navigational electrode positioning features 126 can be formed as recessed pockets, in some embodiments, as further discussed herein. The navigational electrode positioning features 126 can be sized to hold a respective one of the navigational electrodes 120. Accordingly, each one of the navigational electrodes 120 can be held in a fixed position with respect to one another. In some embodiments, the navigational electrodes 120 can be circumferentially disposed about the navigational assembly base 142. For example, the navigational electrodes 120 can be circumferentially spaced about the navigational assembly base 142. In some embodiments, a circumferential spacing between each of the navigational electrodes 120 can be equal.

In some embodiments, the navigational assembly base 142 can include a magnetic position sensor positioning feature, which is further discussed herein. In an example, the magnetic position sensor positioning feature can be formed on an outer surface of the navigational assembly base 142 and can be a recessed area around which the magnetic position sensor is wound. The magnetic position sensor positioning feature and the navigational electrode positioning features 126 can allow for the navigational electrodes 120 and the magnetic position sensor 116 to be positioned in a known spatial relationship with respect to one another. For example, the navigational assembly base 142 can be manufactured to include the positional features at predetermined locations.

Additionally, the positional features can be positional features that can be sized to securely hold the navigational electrodes 120 and/or the magnetic position sensor 116 in known positions. For example, in some approaches, during manufacturing, positional sensors can be placed on an outer surface of a medical device and the medical device may not include positional features that can aid in the placement of positional sensors. Thus, the positional sensors can be placed in different positions on each medical device, which creates the need for calibrating the positional sensors on each medical device. For example, two uncalibrated medical devices may provide different signals from either the navigational electrodes and/or magnetic position sensors disposed on the medical device because the navigational electrodes and/or magnetic position sensors can be positioned differently with respect to each device. Accordingly, some embodiments of the present disclosure can provide for navigational electrode positioning features and magnetic position sensor positioning features that can enable accurate and consistent placement of navigational electrodes and/or magnetic position sensors, thereby reducing or eliminating a calibration step. In an example, the navigational assembly base 142 can hold the navigational electrodes 120 and the magnetic position sensor 116 in tight tolerances with respect to one another so that calculations combining the data sets generated via the navigational electrodes 120 and the magnetic position sensor 116 can have a high confidence.

In some embodiments, the medical device can include a central mounting bore 128, which can extend through the navigational assembly 140 and can aid in connecting the navigational assembly 140 to the elongate shaft 112. The central mounting bore 128 is further discussed herein.

In some embodiments, a flexible tip assembly 130 can be connected to a distal end of the medical device 110 and/or to a distal end of the central mounting bore 128 and/or distal end of the navigational assembly 140. The flexible tip assembly 130 can include a tip 132 (e.g., atraumatic tip) in some embodiments. The flexible tip assembly 130 can include, for example, a flexible tip electrode from a FlexAbility™ irrigated ablation catheter manufactured by St. Jude Medical, Inc. of St. Paul, Minn. Additional details regarding a flexible electrode tip assembly may be found in, for example, U.S. Pat. No. 8,187,267 B2, United States patent application publication no. US 2010/0152731 A1, U.S. patent application Ser. No. 14/724,169, and U.S. patent application Ser. No. 14/213,289, each of which is hereby incorporated by reference as though fully set forth herein. However, in some embodiments, the medical device 110 can include other types of tip assemblies.

In some embodiments, an additional ring electrode 114-3 can be disposed between the navigational assembly 140 and the flexible tip assembly 130. As previously discussed with reference to ring electrodes 114-1, 114-2, the ring electrode 114-3 can be used for navigational and/or diagnostic purposes.

Figure 3:
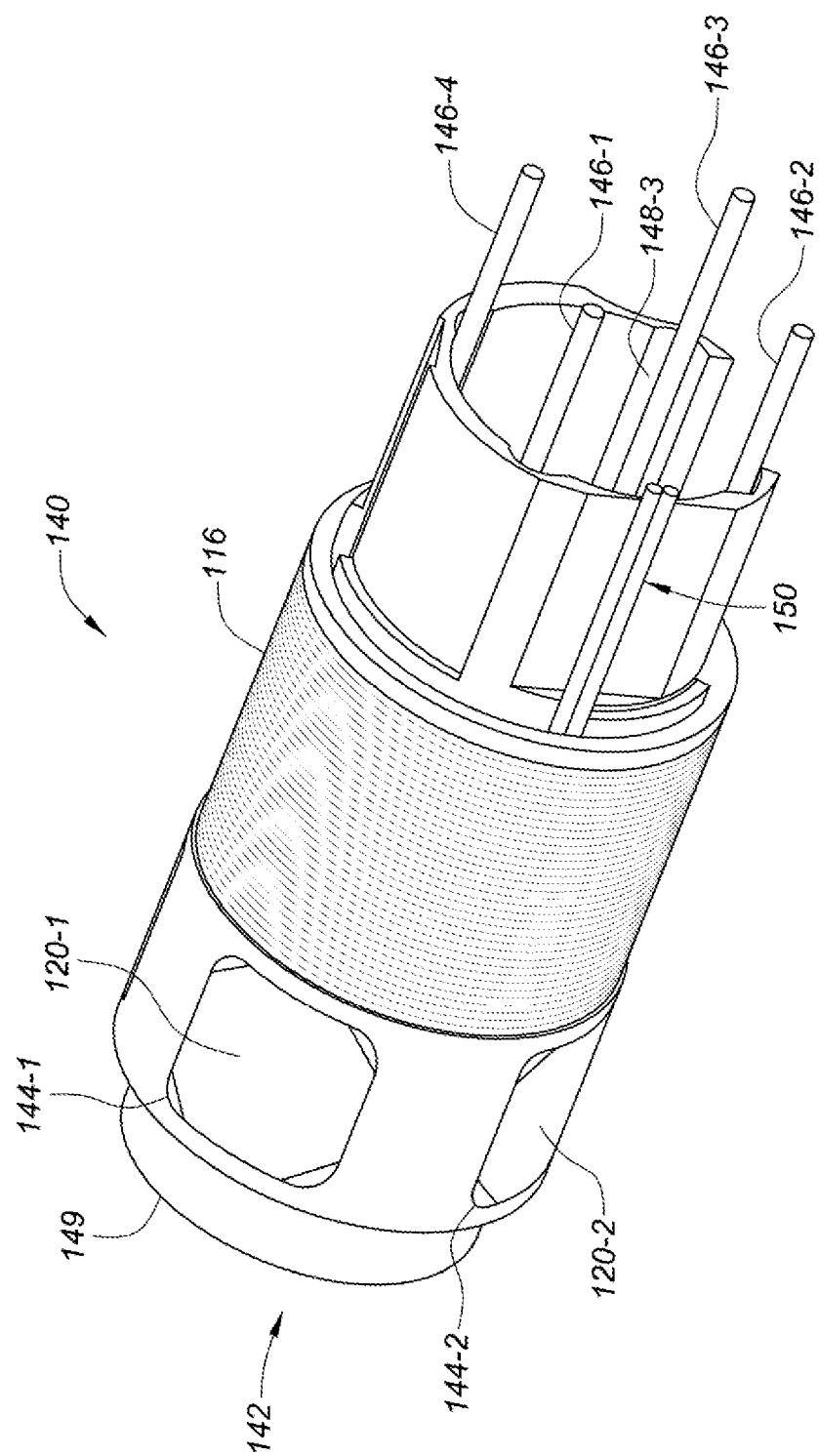
FIG. 3 is an isometric side, top, and rear view of the navigational assembly depicted in FIG. 2 that includes navigational electrodes and a magnetic position sensor, in accordance with embodiments of the present disclosure.

FIG. 3 is an isometric side, top, and rear view of a navigational assembly 140 that includes navigational electrodes 120-1, 120-2, hereinafter generally referred to as navigational electrodes 120, and a magnetic position sensor 116, in accordance with embodiments of the present disclosure. A third navigational electrode 120-3 and fourth navigational electrode 120-4 are hidden from view. The navigational assembly 140 can include features similar to those discussed in relation to FIG. 2. In some embodiments, the navigational assembly 140 can include a proximal end and a distal end and can extend along a longitudinal axis. The navigational assembly 140 can define a central lumen that extends along the longitudinal axis and passes through the navigational assembly 140. In some embodiments, the navigational assembly 140 and/or the navigational assembly base 142 can be cylindrical in shape and can have a circular, square, triangular, etc. cross-section defined by a plane transverse to the longitudinal axis of the navigational assembly 140.

In some embodiments, the navigational electrodes 120 can be disposed in navigational electrode positioning features 144-1, 144-2. In some embodiments, the navigational electrode positioning features 144-1, 144-2 can be sized such that upon insertion of a navigational electrode 120 into a respective electrode positioning feature 144, the navigational electrodes 120 are held in fixed positions (e.g., with aid of an adhesive) and are not able to move longitudinally or circumferentially. As further described herein, an electrode wire lumen can extend through a wall of the navigational assembly base 142 between the navigational positioning feature 144 and the central lumen that extends along the longitudinal axis and passes through the navigational assembly base 142. In some embodiments, electrode wires can extend through the central lumen and through the electrode wire lumen in order to electrically couple the navigational electrodes 120 to a medical positioning system 22. For example, electrode wires 146-1, 146-2, 146-3, 146-4 can extend through the central lumen and through the electrode wire lumens, connecting the navigational electrodes 120 to the medical positioning system 22.

In some embodiments, wire grooves 148 can extend along an inner wall of the navigational assembly 140. The electrode wires 146 can be positioned in the wire grooves 148, in some embodiments. The wire grooves 148 can extend proximally from each electrode wire lumen along the inner wall of the navigational assembly 140.

Figure 4:
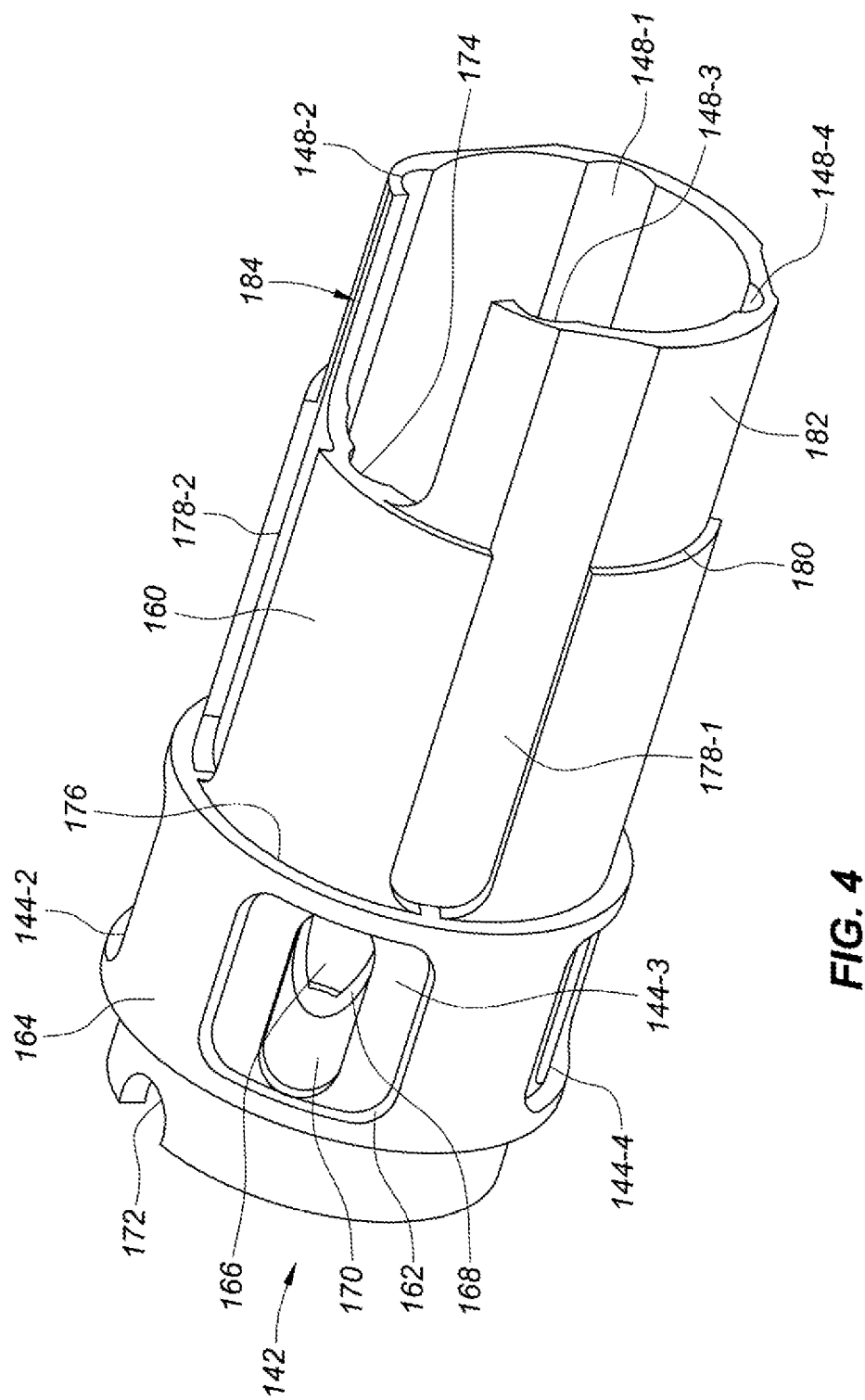
FIG. 4 is an isometric side, bottom, and rear view of the navigational assembly base depicted in FIG. 2 that includes navigational electrode positioning features and a magnetic position sensor positioning feature, in accordance with embodiments of the present disclosure.

FIG. 4 is an isometric side, bottom, and rear view of a navigational assembly base 142 depicted in FIG. 2 that includes navigational electrode positioning features 144-2, 144-3, 144-4 (navigational electrode positioning feature 144-1 is hidden from view) and a magnetic position sensor positioning feature 160, in accordance with embodiments of the present disclosure. In some embodiments, as discussed herein, the navigational electrode positioning features 144 can be circumferentially disposed about the navigational assembly base 142. As depicted in FIG. 4, the navigational electrode positioning features 144 can be recessed pockets defined in an outer surface of the navigational assembly base 142.

In some embodiments, the navigational electrode positioning features 144 can be defined in a positional ring 164 that circumferentially extends around an exterior surface of the navigational assembly base 142. The positional ring 164 can have a greater diameter than other portions of the navigational assembly base 142, allowing for the recessed pockets that form the navigational electrode positioning features 144 to be formed in the positional ring 164 while maintaining an adequately thick wall between the recessed pocket and the central lumen of the navigational assembly base 142. In some embodiments, the positional ring 164 can define the electrode positioning features 144. In some embodiments, the positional ring 164 can include an inner circumferential wall 162 that surrounds the electrode positioning feature 144-3. Although the electrode positioning features 144 are depicted as square with rounded corners, the electrode positioning features 144 can be any type of shape, as discussed herein.

In some embodiments, an electrode wire lumen 166 can extend through a sidewall of the navigational assembly base 142 from the central lumen to the electrode positioning feature 144-3. In some embodiments, the electrode wire lumen 166 can be surrounded by a beveled wall 168, as depicted in FIG. 4. Although the wall 168 is depicted in FIG. 4 as being beveled, the wall can also be chamfered and/or radiused to help with introduction of an electrode wire into the central lumen of the navigational assembly base 142. For example, the electrode wire can enter the central lumen at less of an angle by beveling the wall 168 that defines the electrode wire lumen 166.

In some embodiments, an adhesive pocket 170 can be formed within a base of the recessed pocket of the electrode positioning feature 144-3. In an example, the adhesive pocket can extend from a proximal wall to a distal wall that define the electrode positioning feature 144-3 and can surround the electrode wire lumen 166. The adhesive pocket 170 can provide a space for adhesive to collect if adhesive is used to secure the navigational electrodes in the electrode positioning features 144. In some embodiments, because the adhesive pocket 170 surrounds the electrode wire lumen 166, additional adhesive can surround the electrode wire lumen 166 and an electrode wire disposed in the electrode wire lumen 166, thus helping to secure the electrode wire in the electrode wire lumen 166.

As depicted in FIG. 4, an inner wall of the navigational assembly base 142 that defines the central lumen can further define wire grooves 148-1, 148-2, 148-3, 148-4, hereinafter generally referred to in the plural as wire grooves 148, which longitudinally extend along the inner wall. In some embodiments, a radial depth of the wire grooves 148 can be less than a width of the electrode wires. In some embodiments, each of the wire grooves can be longitudinally aligned with each of the electrode wire lumens 166. Thus, the navigational assembly base can include a same number of wire grooves 148 as electrode wire lumens 166. In some embodiments, the navigational assembly base 142 can include additional wire grooves. For example, additional wire grooves can be included in the inner wall of the navigational assembly base 142 when additional electrical components are mounted distally with respect to the navigational assembly 140. In some embodiments, as discussed herein, a ring electrode 114-3 can be mounted distally with respect to the navigational assembly 140.

In some embodiments, a distal edge 149 of the navigational assembly base 142 can define a distal electrode wire lumen 172. The distal electrode wire lumen 172 can extend proximally into the navigational assembly base 142 and can provide room for a wire to extend from the ring electrode 114-3 into the central lumen of the navigational assembly 140. In some embodiments, a longitudinal length of the distal electrode groove 172 can be less than a width of the wire. In some embodiments, an additional wire groove 174 can be defined by the inner wall of the navigational assembly 140. The additional wire groove 174 can be longitudinally aligned with the distal electrode groove 172 in some embodiments, providing a pathway for an electrode wire to pass through the navigational assembly 140.

In some embodiments, as discussed herein, the navigational assembly base 142 can include a magnetic position sensor positioning feature 160. The magnetic position sensor positioning feature 160 can be located proximally with respect to the navigational electrode positioning features 144. In some embodiments, the positional ring 164 can form a distal positioning lip 176, which in part defines the magnetic position sensor positioning feature 160. In some embodiments, the magnetic position sensor positioning feature 160 can extend proximally from the positioning lip 176 and can include a cylindrical outer surface upon which the magnetic position sensor 116 can be wound. As depicted in FIG. 3, sensor wires 150 can be electrically coupled with the magnetic position sensor 116 and can extend proximally along the navigational assembly 140.

In some embodiments, one or more longitudinally extending field concentrating antenna grooves 178-1, 178-2 can be formed in the outer surface of the navigational assembly base 142. Field concentrating antennas can be disposed in the longitudinally extending field concentrating antenna grooves 178-1, 178-2, which can aid in concentrating a magnetic field with respect to the magnetic position sensor, as discussed in relation to PCT application no. PCT/US2016/022669, entitled "Field Concentrating Antennas for Magnetic Position Sensors," hereby incorporated by reference in its entirety as though fully set forth herein.

In some embodiments, the navigational assembly base 142 can include a proximal attachment portion 182. The proximal attachment portion 182 can include a smaller diameter than the magnetic position sensor positioning feature 160 and can extend proximally with respect to the magnetic position sensor positioning feature 160, creating a proximal positioning lip 180. In some embodiments, the navigational assembly base 142 can be slid into a distal end of an elongate shaft up until the proximal positioning lip 180.

In some embodiments, a proximal end of the navigational assembly base 142 can include an alignment slot 184. The alignment slot 184 can be defined by a u-shaped cutout in the proximal end of the navigational assembly base 142. In some embodiments, the alignment slot 184 can extend distally through a sidewall of the navigational assembly base 142. The alignment slot 184 may not be u-shaped in some embodiments and may include a squared distal end in some embodiments.

Figure 5:
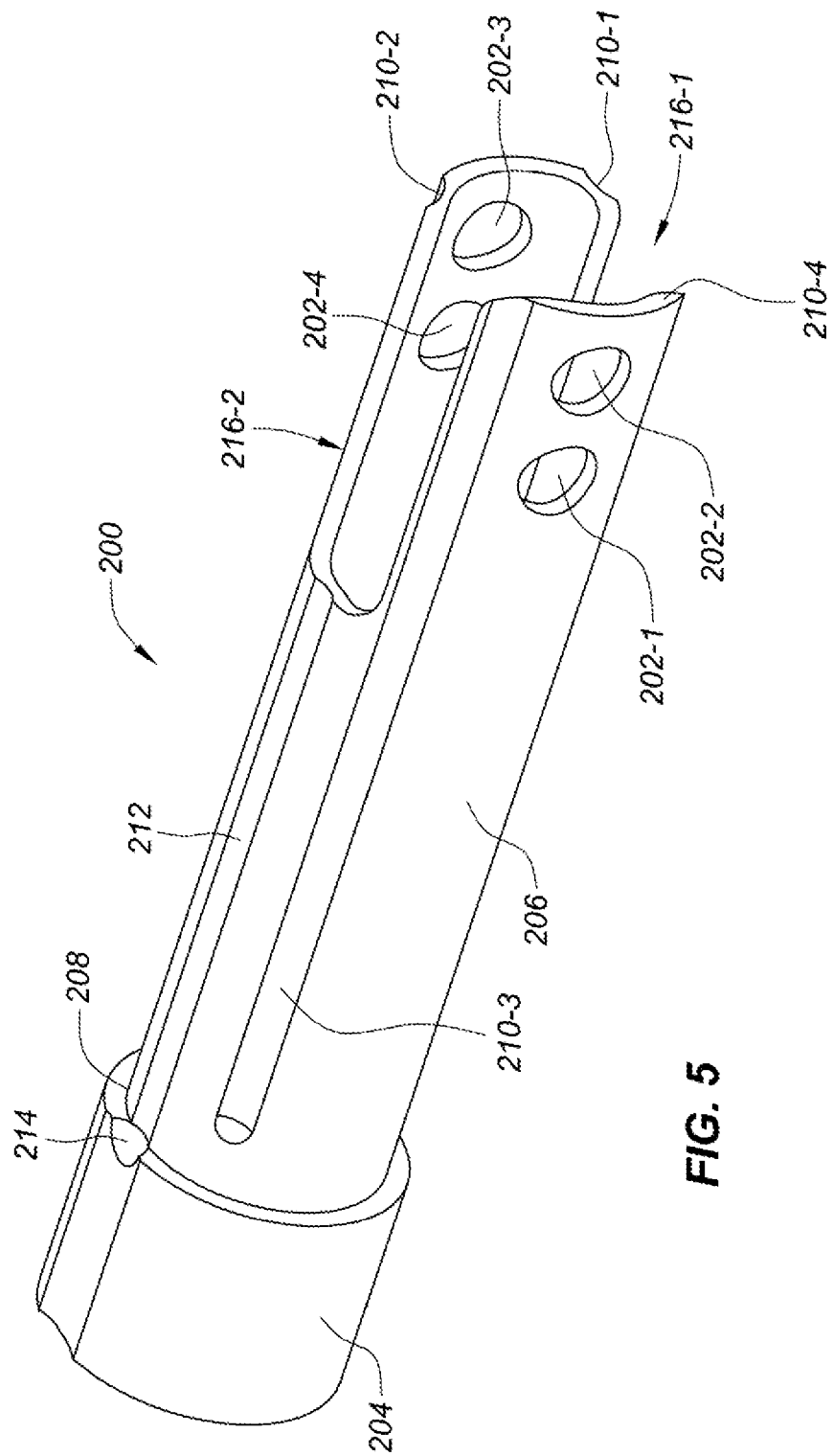
FIG. 5 is an isometric side, bottom, and rear view of a central mounting bore, in accordance with embodiments of the present disclosure.

FIG. 5 is an isometric side, bottom, and rear view of a central mounting bore 200, in accordance with embodiments of the present disclosure. In some embodiments, the central mounting bore 200 can include a proximal end and a distal end and can extend along a longitudinal axis. The central mounting bore 200 can include a distal mounting portion 204 and an elongate body portion 206. In some embodiments, the distal mounting portion 204 can have a larger diameter than the elongate body portion 206, creating a bore positioning lip 208.

In some embodiments, an outer diameter of the elongate body portion 206 can be smaller than an inner diameter of the navigational assembly base discussed herein. Accordingly, the elongate body portion 206 of the central mounting bore can be inserted through the central lumen formed by the navigational assembly. In some embodiments, the elongate body portion 206 can be slid through the central lumen formed by the navigational assembly such that the distal edge 149 of the navigational assembly base 142 abuts the bore positioning lip 208.

The central mounting bore 200 can include wire grooves 210-1, 210-2, 210-3, 210-4 and an additional wire groove 212. In some embodiments, upon insertion of the elongate body portion 206 through the central lumen of the navigational assembly, the wire grooves 210-1, 210-2, 210-3, 210-4 can be aligned with the wire grooves 148-1, 148-2, 148-3, 148-4 depicted in FIG. 4, respectively, to form wire lumens through which wires pass that electrically couple the navigational electrodes of the navigational assembly 140 with the medical positioning system 22. Likewise, the additional wire groove 212 can be aligned with the additional wire groove 174 depicted in FIG. 4 to form a wire lumen through which one or more wires pass that electrically couple the ring electrode 114-3 to the medical positioning system 22.

In some embodiments, the additional wire groove 174 can extend longitudinally from the elongate body portion 206 to a distal end of the distal mounting portion 204. In some embodiments, the wire groove 174 can be of a constant depth between the portion of the wire groove 174 located on the elongate body portion 206 and the portion located on the distal mounting portion 204. In some embodiments, a transition recess 214 can be formed between the portions of the wire groove 174 located on the elongate body portion 206 and the distal mounting portion 204.

In some embodiments, the central mounting bore 200 can define mounting holes 202-1, 202-2, 202-3, 202-4, generally referred to herein in the plural as mounting holes 202, in a proximal portion of the central mounting bore 200, for example, in a proximal portion of the elongate body portion 206. In some embodiments, although four mounting holes 202 are depicted, more than four or less than four mounting holes can be formed in the proximal portion of the central mounting bore 200. As depicted, a first mounting hole 202-1 and second mounting hole 202-2 are diametrically opposed to a third mounting hole 202-3 and a fourth mounting hole 202-4, respectively. In some embodiments, one or more mounting pins can extend through the mounting holes 202 in order to secure the central mounting bore 200 to a distal end of an elongate shaft (e.g., catheter). In some embodiments, the mounting holes 202 can provide an area for glue to accumulate when mounting the central mounting bore 200 to the distal end of the elongate shaft.

In some embodiments, the central mounting bore 200 can include one or more alignment slots 216-1, 216-2. For example, the proximal end of the elongate body portion can include the alignment slots 216-1, 216-2. In some embodiments, a proximal portion can define a first alignment slot 216-1 that extends longitudinally towards a distal end of the central mounting bore 200 and a second alignment slot 216-2 that is diametrically opposed to the first alignment slot 216-1. The alignment slots 216-1, 216-2 can be u-shaped, as depicted, but can also be of another shape such as a square, rectangle, etc. In some embodiments, a distal end of the elongate shaft 112 can include a mounting feature that is complementary to the alignment slots 216-1, 216-2. The alignment feature can be inserted into the alignment slots 216-1, 216-2 to ensure that the central mounting bore 200 is correctly aligned with the elongate shaft 112. For example, this can be beneficial when the elongate shaft 112 is configured to deflect in a particular direction.

In some embodiments, the central mounting bore 200 can act as a radiofrequency cover. For example, where the medical device 110 includes an ablation element disposed at a distal end, radiofrequency signals can be transmitted to the ablation element via wires that extend through the central mounting bore and electrically connect the ablation element to a radiofrequency generator. In some embodiments, the radiofrequency signals can cause noise in electrical signals being transmitted from surrounding electrical components. For example, signals being transmitted from the ring electrodes 114, the navigational electrodes 120, and/or the magnetic position sensor 116, depicted in FIG. 2, can be affected by noise caused by the transmission of radiofrequency signals to the ablation element. As such, the central mounting bore 110 can act as a radiofrequency cover in some embodiments and can be made from a material that can block and/or deflect the radiofrequency waves being transmitted to the ablation element. In some embodiments, the central mounting bore 110 can be formed from a polymer. In an example, the central mounting bore 110 can be formed from acrylonitrile butadiene styrene (ABS), polyether ether ketone (PEEK), polycarbonate, amorphous thermoplastic polyetherimide (PEI), such as ULTEM™.

Figure 6A:
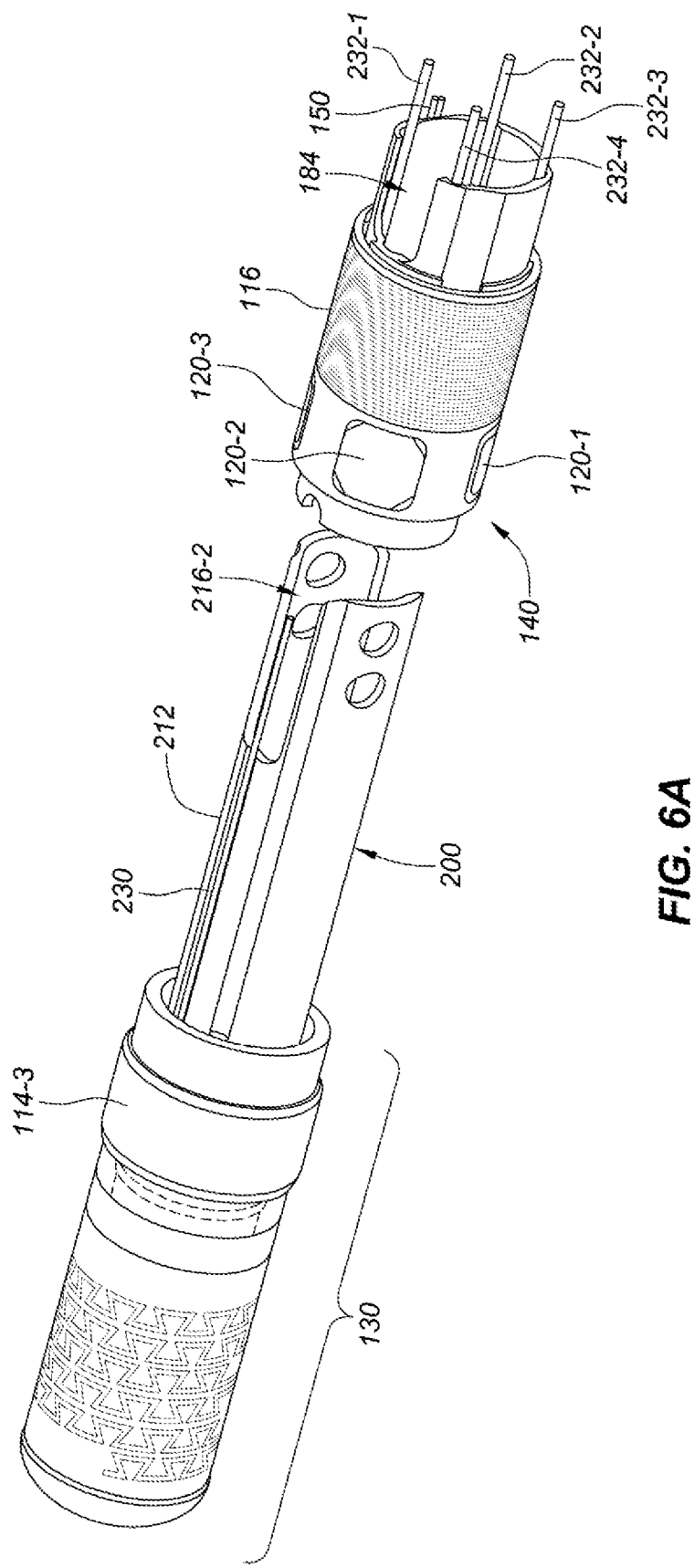
FIG. 6A is an isometric side, bottom, and rear view of the navigational assembly depicted in FIG. 3, the central mounting bore depicted in FIG. 5, and the flexible tip assembly depicted in FIG. 2 in a pre-assembled state, in accordance with embodiments of the present disclosure.

FIG. 6A is an isometric side, bottom, and rear view of the navigational assembly 140 depicted in FIG. 3, the central mounting bore 200 depicted in FIG. 5, and a flexible tip assembly 130 depicted in FIG. 2 in a pre-assembled state, in accordance with embodiments of the present disclosure. In some embodiments, the distal end of the central mounting bore 200 (e.g., distal mounting portion 204) can be connected to the proximal end of the flexible tip assembly 130. As depicted, an electrode wire 230 extends from the additional electrode 114-1 proximally along the central mounting bore 200 in the additional wire groove 212.

As previously discussed, the navigational assembly 140 can include the navigational electrodes 120, which can be electrically coupled to the medical positioning system 22 via electrode wires 232-1, 232-2, 232-3, 232-4. The navigational assembly 140 can further include the magnetic position sensor 116, which can be electrically coupled to the medical positioning system 22 via sensor wires 150.

As depicted in FIG. 6A, the navigational assembly 140 has not been inserted on to the central mounting bore 200. In some embodiments, the navigational assembly can be slid distally from the position depicted in FIG. 6A such that the proximal portion of the central mounting bore is inserted through the central lumen defined by the navigational assembly 140.

Figure 6B:
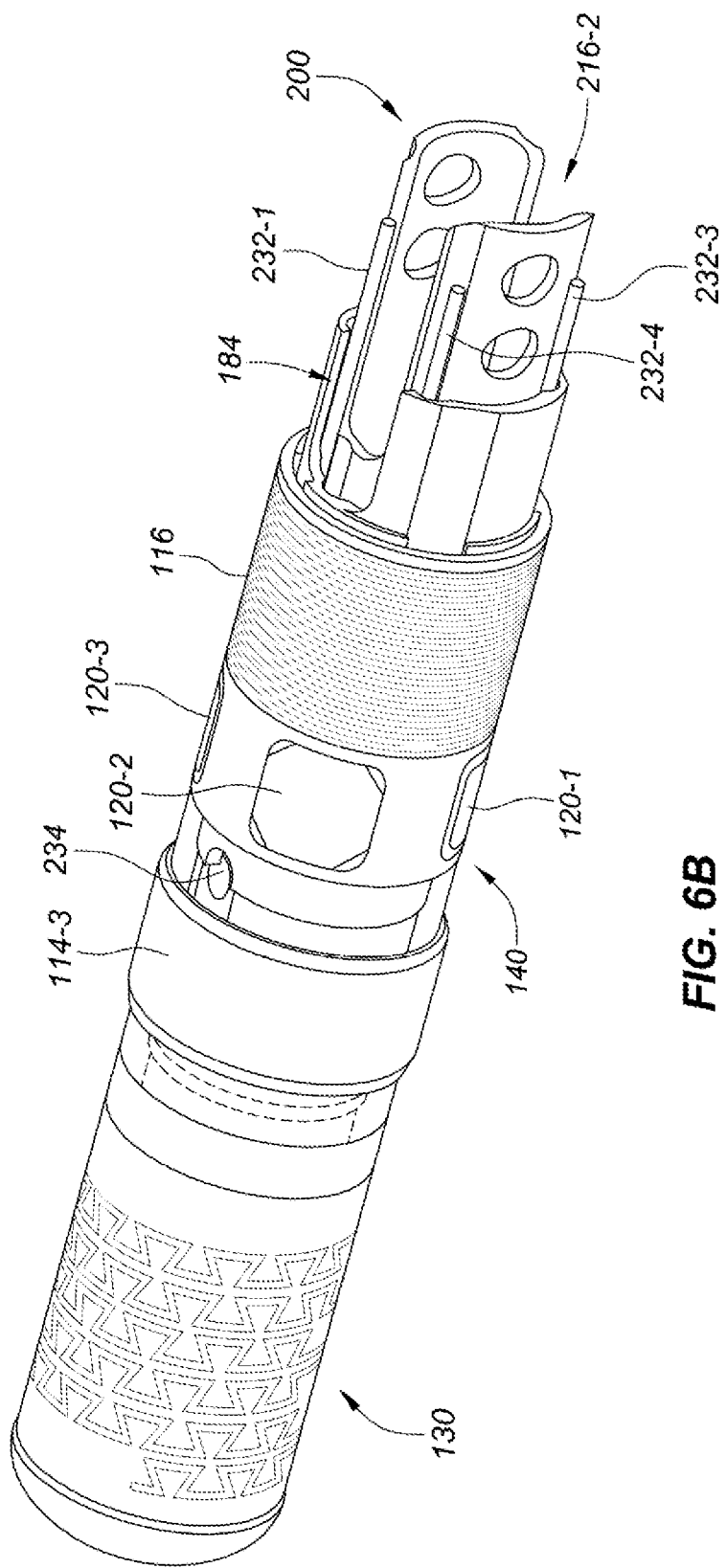
FIG. 6B is an isometric side, bottom, and rear view of the navigational assembly, the central mounting bore, and the flexible tip assembly depicted in FIG. 6A in an assembled state, in accordance with embodiments of the present disclosure.

FIG. 6B is an isometric side, bottom, and rear view of the navigational assembly 140, the central mounting bore 200, and the flexible tip assembly 130 depicted in FIG. 6A in an assembled state, in accordance with embodiments of the present disclosure. As depicted, the proximal portion of the elongate mounting bore 200 has been inserted through the central lumen formed in the navigational assembly 140. The distal edge 149 can abut the bore positioning lip 208 in some embodiments, forming an electrode wire thru hole 234 through which the electrode wire 230 associated with the additional electrode 114-3 can pass. The thru hole 234 can be formed via a distal electrode wire lumen, as discussed in relation to FIG. 4, and the transition recess 214, as depicted in FIG. 5.

In some embodiments, upon assembly of the flexible tip assembly 130, the navigational assembly 140, and the central mounting bore 200, a seal can be created between the flexible tip assembly 130 and the navigational assembly 140. For example, a seal can be created between the distal edge 149 and the bore positioning lip 208. In some embodiments, an adhesive can be applied around a joint created between the distal edge 149 and the bore positioning lip 208. In some embodiments, adhesive can be applied along a mating surface between the navigational assembly 140 and the central mounting bore 200.

Figure 7A:
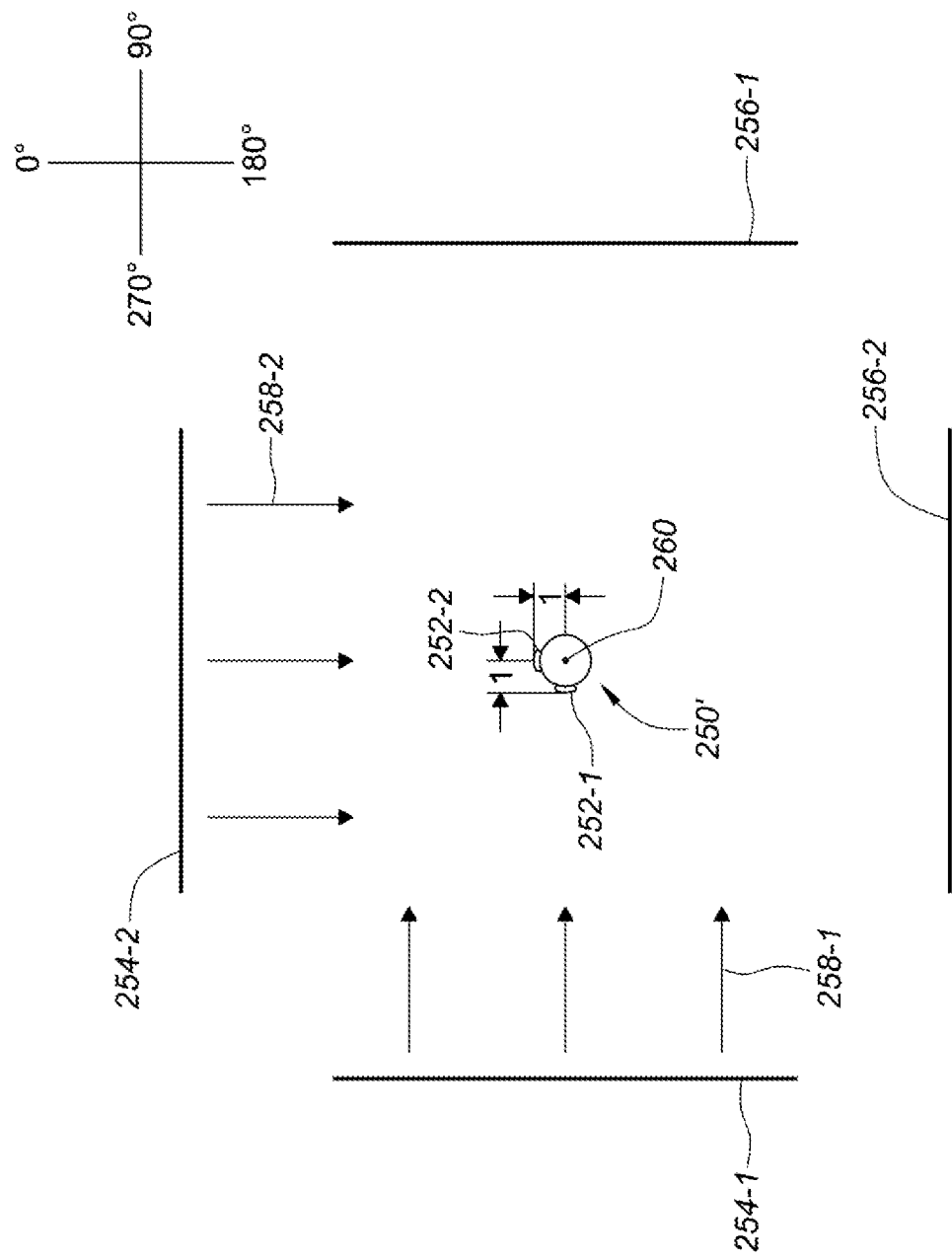
FIG. 7A depicts a medical device with a first navigational electrode and second navigational electrode disposed at an approximately zero degree rotation in a dual source electrical field, in accordance with embodiments of the present disclosure.

FIG. 7A depicts a medical device 250 with a first navigational electrode 252-1 and second navigational electrode 252-2, hereinafter generally referred to in the plural as navigational electrodes 252, disposed at a zero degree rotation in a dual source electrical field, in accordance with embodiments of the present disclosure. Embodiments of the present disclosure can provide for sensing a position and orientation of a medical device 250 with six degrees of freedom. In an example, a medical device 250, similar to and/or containing similar features as those discussed in relation to FIGS. 2 to 6B can include navigational electrodes 252, which can be circumferentially spaced about the medical device similar to electrodes 120 depicted and described in relation to FIG. 2A to FIG. 6B. In some embodiments, the navigational electrodes 252 can be circumferentially spaced about a particular point on a longitudinal axis associated with the medical device 250. Although two navigational electrodes 252 are depicted in FIG. 7A, fewer than two navigational electrodes 252 or greater than two navigational electrodes 252 (e.g., four navigational electrodes) can be include on the medical device 250.

The medical device 250 can be positioned in a dual source electrical field generated by a first current source 254-1 producing a first electrical field 258-1 and a second current source 254-2 producing a second electrical field 258-2, hereinafter generally referred to in the plural as current sources 254 and electrical fields 258, respectively. The first electrical field 258-1 can be generated between the first current source and a first current receiver 256-1, which can both be patches, such as that shown above and described in relation to FIGS. 12 and 13, in an example. The second electrical field 258-2 can be generated between the second current source and a second current receiver 256-2, which can also both be patches, in an example. In some embodiments, as the medical device 250 rotates, a determined position associated with each of the navigational electrodes 252 can shift as each of the navigational electrodes 252 rotates away from one of the current sources 254. By measuring the electrode shift (e.g., measured from a reference position 260), a rotation of the medical device 250 can be determined. In some embodiments, the electrode shift associated with each navigational electrode 252 can be measured from a center axis of the medical device 250, as depicted in FIG. 7A. However, the electrode shift can be measured with respect to other reference positions associated with the medical device (e.g., a position associated with each navigational electrode).

In an example, the reference position 260 can be determined from a signal generated by a magnetic position sensor disposed on the medical device 250 (e.g., magnetic position sensor 116). The signal generated by the magnetic position sensor 250 is not subject to shift and/or drift, which can be the case with signals associated with navigational electrodes 252, resulting in an accurate determination of a reference position 260 from which the shift can be measured.

As depicted in FIG. 7A, the medical device is depicted at a rotation of approximately zero degrees. At the zero degree rotation, the first navigational electrode 252-1 is positioned on a side of the medical device 250 towards the first current source and the second navigational electrode 252-2 is positioned on a side of the medical device 250 towards the second current source 258-2. Accordingly, the determined position associated with each of the navigational electrodes 252 is unshifted.

In some embodiments, a particular degree of rotation can be associated with the unshifted positions of the navigational electrodes 252. For instance, the particular degree of rotation can be determined based on a shift state of the navigational electrodes 252 (e.g., whether or not the determined position associated with each of the navigational electrodes 252 has been shifted). As depicted in FIG. 7A, a distance between the reference position 260 and the first navigational electrode 252-1 is one and a distance between the reference position 260 and the second navigational electrode 252-2 is 1, indicating that neither of the determined positions associated with each of the navigational electrodes 252 has been shifted.

Figure 7B:
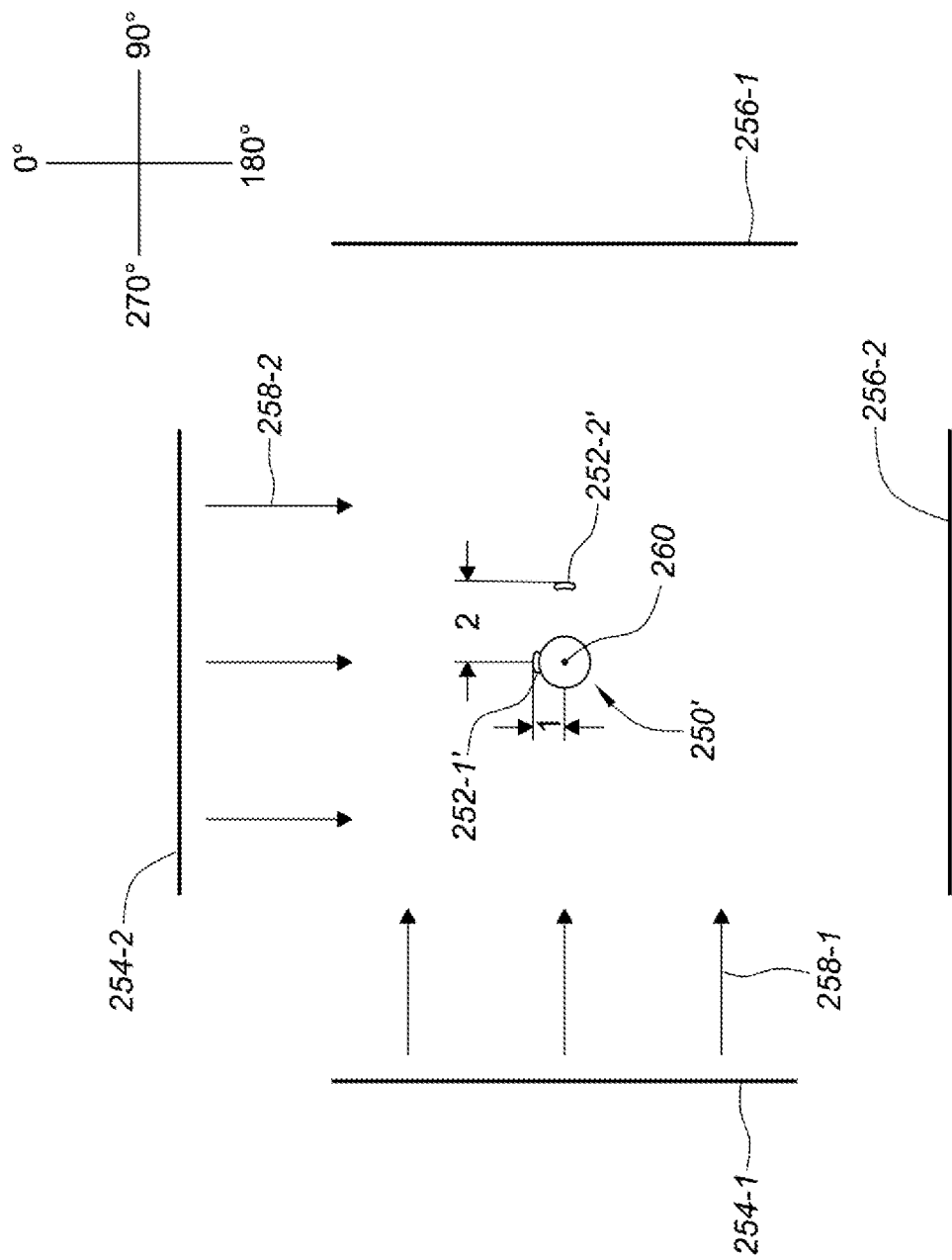
FIG. 7B depicts the medical device in FIG. 7A with first navigational electrode and second navigational electrode disposed at an approximately 90 degree rotation in the dual source electrical field, in accordance with embodiments of the present disclosure.

FIG. 7B depicts a medical device 250' with a first navigational electrode 252-1' and second navigational electrode 252-2', hereinafter generally referred to in the plural as navigational electrodes 252', disposed at an approximately 90 degree rotation in a dual source electrical field, in accordance with embodiments of the present disclosure. In contrast to FIG. 7A, the medical device 250' has been rotated (e.g., rolled about the reference position 260) 90 degrees clockwise. As depicted, the determined position associated with the second navigational electrode 252-2' has been shifted, because the second navigational electrode 252-2' is now disposed on an opposite side of the medical device 250' with respect to the first current source 254-1.

In some embodiments, a first electrical field 258-1 can be generated between a pair of patches. For example, current can flow between a first current source 254-1 (e.g., driving patch) and a first current receiver 256-1 (e.g., reading patch), between which the medical device 250' is disposed. As current passes from the first current source 254-1 to the first current receiver 256-1, a low current area is formed on the side of the medical device 250' opposite the first current receiver 256-1 (e.g., on the side which the second navigational electrode 252-2' is disposed). For example, the low current area is shielded by the medical device 250', causing a current received by the second navigational electrode 252-2' (e.g., spot electrode) to be reduced. Accordingly, a current received by the second navigational electrode 252-2' is lower than when the second navigational electrode 252-2' is disposed directly in the first electrical field 258-1. Thus, a position of the second navigational electrode 252-2' calculated based on the lower navigational current is shifted away from the reference position 260 (e.g., centerline of the catheter) and away from the first current source 254-1.

As depicted in FIG. 7B, a distance between the reference position 260 and the first navigational electrode 252-1' is one and a distance between the reference position 260 and the second navigational electrode 252-2' is 2, indicating that the determined position associated with the first navigational electrode 252-1' is unshifted and the determined position associated with the second navigational electrode 252-2' is shifted. Accordingly, a determination can be made that the second navigational electrode 252-2' is disposed on an opposite side of the medical device 250' from one of the current sources 254, while the first navigational electrode 252-1' is disposed on a same side of the medical device 250' as one of the current sources 254. Accordingly, a determination that the medical device 250' was rolled 90 degrees counterclockwise can be made based on the shift associated with the navigational electrodes 252'. The determination can be made that the medical device 250' was rolled 90 degrees clockwise and not 90 degrees counterclockwise, as this would result in a different shift associated with the determined positions of each of the navigational electrodes 252', as further discussed in relation to FIG. 7D.

Figure 7C:
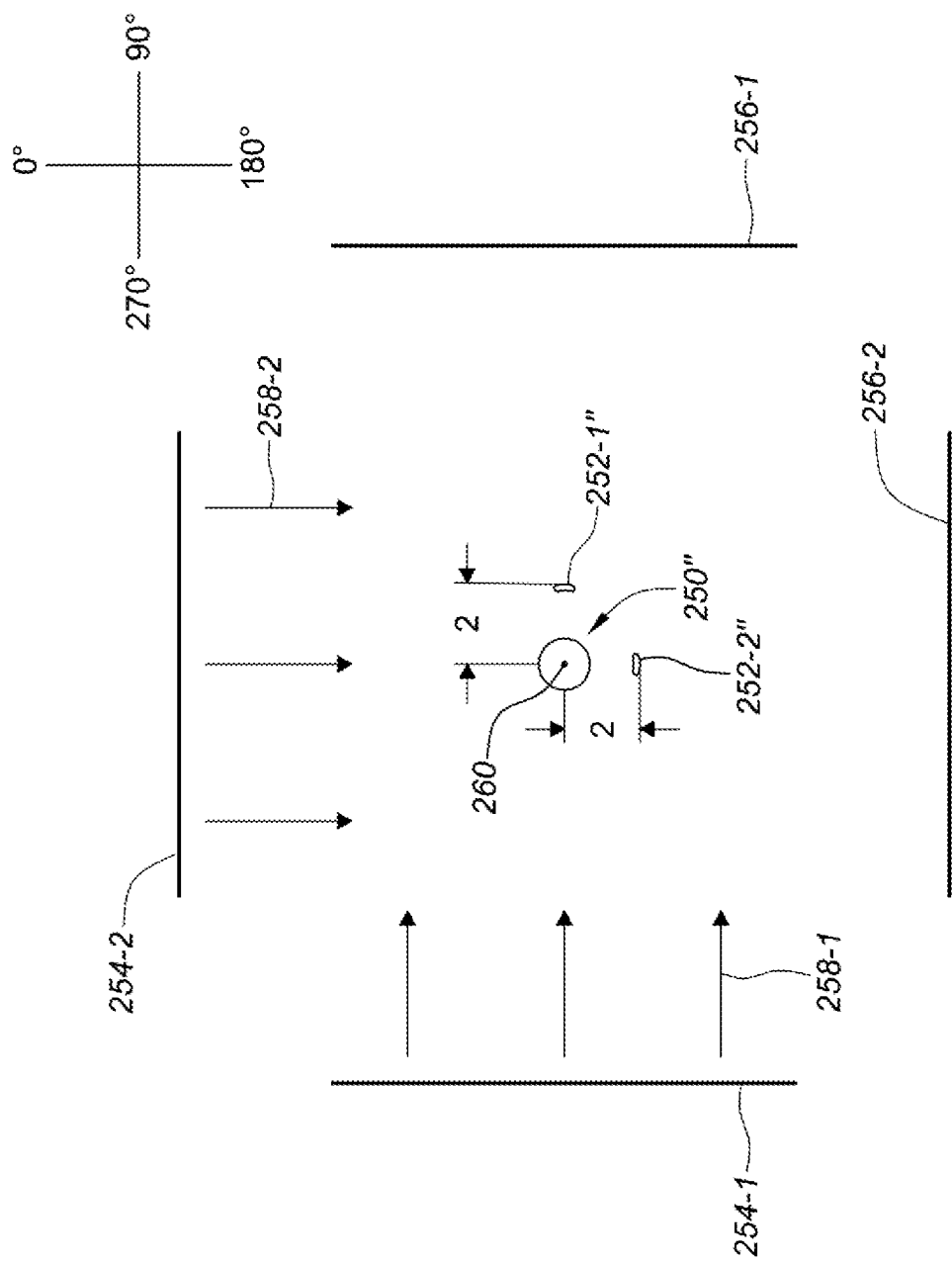
FIG. 7C depicts the medical device in FIG. 7A with first navigational electrode and second navigational electrode disposed at an approximately 180 degree rotation in the dual source electrical field, in accordance with embodiments of the present disclosure.

FIG. 7C depicts a medical device 250" with a first navigational electrode 252-1" and second navigational electrode 252-2", hereinafter generally referred to in the plural as navigational electrodes 252", disposed at an approximately 180 degree rotation in a dual source electrical field, in accordance with embodiments of the present disclosure. In contrast to FIG. 7A, the medical device 250" has been rotated (e.g., rolled about the reference position 260) 180 degrees clockwise. As depicted, the determined position associated with the first navigational electrode 252-1" and the second navigational electrode 252-2" have been shifted, because the first and second navigational electrodes 252" are now disposed on opposite sides of the medical device 250" with respect to the first current source 254-1 and second current source 254-2, respectively.

As depicted in FIG. 7C, a distance between the reference position 260 and the first navigational electrode 252-1" is two and a distance between the reference position 260 and the second navigational electrode 252-2" is 2, indicating that the determined position associated with the first navigational electrode 252-1" is shifted and the determined position associated with the second navigational electrode 252-2" is shifted. Accordingly, a determination can be made that the first and second navigational electrodes 252" are disposed on opposite sides of the medical device 250" from the first and second current sources 254. Accordingly, a determination that the medical device 250" was rolled 180 degrees counterclockwise can be made based on the shift associated with the navigational electrodes 252".

Figure 7D:
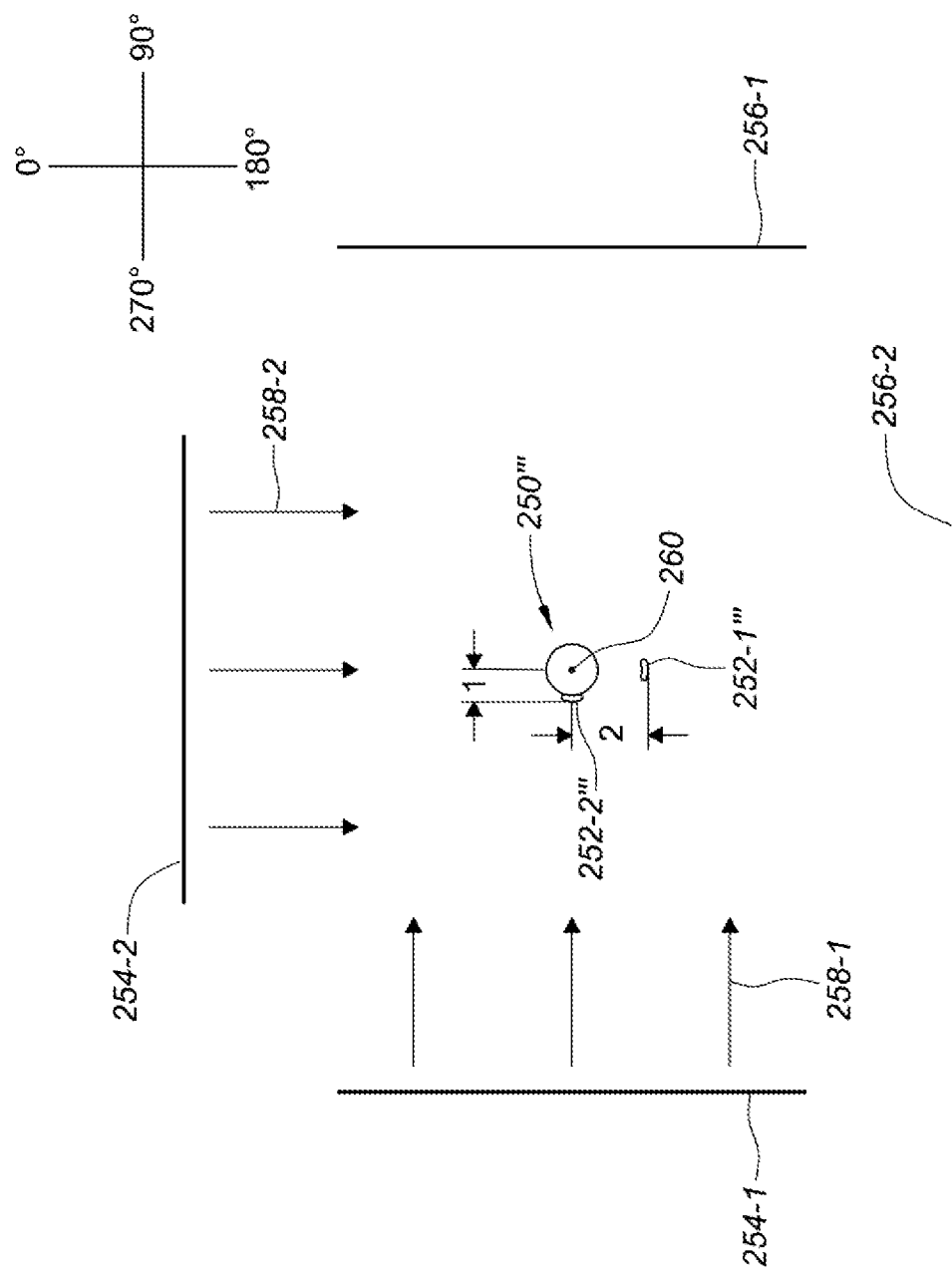
FIG. 7D depicts the medical device in FIG. 7A with first navigational electrode and second navigational electrode disposed at an approximately 270 degree rotation in the dual source electrical field, in accordance with embodiments of the present disclosure.

FIG. 7D depicts a medical device 250''' with a first navigational electrode 252-1''' and second navigational electrode 252-2''', hereinafter generally referred to in the plural as navigational electrodes 252''', disposed at an approximately 270 degree rotation in a dual source electrical field, in accordance with embodiments of the present disclosure. In contrast to FIG. 7A, the medical device 250''' has been rotated (e.g., rolled about the reference position 260) 270 degrees clockwise. As depicted, the determined position associated with the second navigational electrode 252-2''' is unshifted, because the second navigational electrode 252-2''' is now disposed on a same side of the medical device 250''' with respect to the first current source 254-1.

As depicted in FIG. 7B, a distance between the reference position 260 and the first navigational electrode 252-1' is two and a distance between the reference position 260 and the second navigational electrode 252-2''' is 1, indicating that the determined position associated with the first navigational electrode 252-1' is shifted and the determined position associated with the second navigational electrode 252-2''' is unshifted. Accordingly, a determination can be made that the second navigational electrode 252-2''' is disposed on a same side of the medical device 250''' from one of the current sources 254, while the first navigational electrode 252-1' is disposed on an opposite side of the medical device 250''' as one of the current sources 254. Accordingly, a determination that the medical device 250''' was rolled 270 degrees counterclockwise can be made based on the shift associated with the navigational electrodes 252'''. In contrast to FIG. 7B, the determination can be made that the medical device 250''' was rolled 270 degrees clockwise (e.g., 90 degrees counterclockwise) and not 90 degrees clockwise, as this would result in a different shift associated with the determined positions of each of the navigational electrodes 252''', as discussed in relation to FIG. 7C.

FIG. 8 is a method 278 flow diagram for determining a position and orientation of a medical device, in accordance with embodiments of the present disclosure. In some embodiments, the method 278 can include generating an electrical field with a current source and a magnetic field with a magnetic field generator, at block 280. In some embodiments, the current source can be generated via a current source and a current receiver, as discussed herein. The method 278 can include receiving, at block 282, an electrode position signal from an electrode positioned on the medical device, the electrode position signal being generated as a result of the electrode being exposed to the electrical field. In some embodiments, the electrode position signal can be generated by the electrode (e.g., navigational electrode 120-1), as discussed herein, in response to the electrode picking up the electrical field in which the electrode is disposed.

In some embodiments, the method 278 can include receiving a magnetic position signal from a magnetic position sensor positioned on the medical device, the magnetic position signal being generated as a result of the magnetic position sensor being exposed to the magnetic field, at block 284. In some embodiments, the magnetic position signal can be generated by the magnetic position sensor (e.g., magnetic position sensor 116), as discussed herein, in response to the magnetic position sensor picking up the magnetic field in which the magnetic position sensor is disposed.

In some embodiments, the method 278 can include determining a magnetic position based on the magnetic position signal and an electrode position based on the electrode position signal, at block 286. In some embodiments, the magnetic position can be a reference position from which a shift in the electrode position can be determined. For example, in some embodiments, the magnetic position can be associated with a central axis associated with the medical device.

In some embodiments, the method 278 can include determining a rotation of the medical device based on a shift in the electrode position with respect to the magnetic position, at block 288. In an example, as an electrode disposed on the medical device is rotated away from a current source, as a result of the medical device being rotated, a shift can occur in a determined position of the electrode. As the electrode becomes positioned on an opposite side of the medical device with respect to the current source, the shift in the electrode position with respect to the magnetic position can increase. Accordingly, a rotation of the medical device can be determined based on the shift in the electrode position because it will change as the medical device rotates, as further discussed herein.

In some embodiments, the medical device can include a plurality of electrodes circumferentially disposed about a portion (e.g., shaft) of the medical device, as discussed in relation to FIGS. 2 to 7D. The method can include determining a plurality of electrode positions for the plurality of electrodes circumferentially disposed about the portion of the medical device. In some embodiments, the method 278 can include determining a shift in each one of the plurality of electrode positions with respect to the magnetic position. As discussed herein, the magnetic position may not be susceptible to shift and/or drift. Accordingly, the magnetic position can serve as a reference position, in some embodiments.

In some embodiments, the method 278 can include determining rotation of the medical device based on the shift in each one of the plurality of electrode positions. As discussed herein, as a medical device and attached electrode rotates, as discussed in relation to FIGS. 7A to 7B, a position of the electrode determined from a signal received from the electrode can shift, based on where the electrode is located with respect to the medical device and a current source generating an electrical field in which the electrode is disposed. Based on the shift associated with the position of the electrode determined from the signal received from the electrode, the position and orientation of the medical device can be determined with six degrees of freedom. For example, a different electrode shift can be associated with different degrees of rotation (e.g., roll) of the medical device, as discussed herein.

In some embodiments, the position and orientation of the medical device can be used in the calculation of a force vector. For example, in some current systems for force sensing catheters (e.g., ablation catheters), a magnitude of force can be determined, but a force vector cannot be determined because a roll of the catheter cannot be determined. To determine a force vector in three-dimensional space, the position and orientation of the force sensing catheter needs to be determined with six degrees-of-freedom. Accordingly, embodiments of the present disclosure can determine a position and orientation of a medical device with six degrees-of-freedom, allowing for a force vector associated with the medical device (e.g., catheter, force sensing catheter) to be determined. An example of a force sensing catheter can be a TactiCath™ Quartz Ablation Catheter commercially available from St. Jude Medical, Inc., and as generally shown with reference to U.S. Pat. No. 8,567,265 entitled "Triaxial Fiber Optic Force Sensing Catheter," the disclosure of which is incorporated by reference in its entirety. By calculating the roll and knowing the remaining five degrees of freedom (from at least the magnetic sensor), the roll and the magnetic sensor's five degrees of freedom can be combined, owing in part to the precise placement of the navigational electrodes in relation to the magnetic sensor. The precise placement of the navigational electrodes in relation to the magnetic sensor can be made possible by the navigational assembly base and its associated features described herein.

Figure 9:
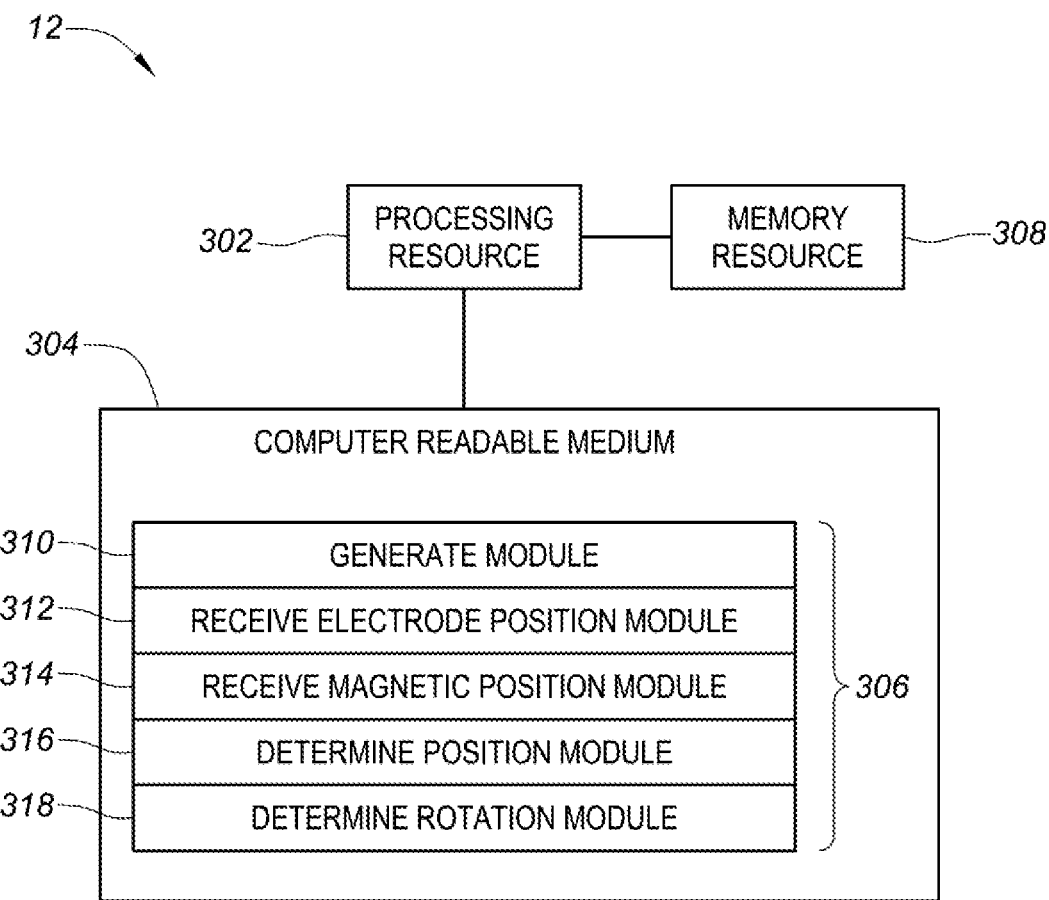
FIG. 9 is a block diagram of an example of a computer-readable medium in communication with processing resources of a computing device, in accordance with embodiments of the present disclosure.

FIG. 9 is a block diagram of an example of a computer-readable medium in communication with processing resources of a computing device, in accordance with embodiments of the present disclosure. The main control 12, as discussed in relation to FIG. 1, can utilize software, hardware, firmware, and/or logic to perform a number of functions. The main control 12 can include a number of remote computing devices.

The main control 12 can be a combination of hardware and program instructions configured to perform a number of functions. The hardware, for example, can include one or more processing resources 302, computer readable medium (CRM) 304, etc. The program instructions (e.g., computer-readable instructions (CRI) 306) can include instructions stored on CRM 304 and executable by the processing resource 302 to implement a desired function (e.g., determine a rotation of the medical device based on a shift in the electrode position with respect to the magnetic position, etc.). The CRI 164 can also be stored in remote memory managed by a server and represent an installation package that can be downloaded, installed, and executed. The main control 12 can include memory resources 308, and the processing resources 302 can be coupled to the memory resources 308.

Processing resources 302 can execute CRI 306 that can be stored on an internal or external non-transitory CRM 304. The processing resources 302 can execute CRI 306 to perform various functions, including the functions as described herein.

A number of modules 310, 312, 314, 316, 318 can be sub-modules or other modules. For example, the determine module 316 and the determine rotation module 318 can be sub-modules and/or contained within a single module. Furthermore, the number of modules 310, 312, 314, 316, 318 can comprise individual modules separate and distinct from one another.

A generate module 310 can comprise CRI 306 and can be executed by the processing resource 302 to generate an electrical field with a current source and a magnetic field with a magnetic field generator. In some embodiments, the electrical field can be generated with one or more current sources and/or one or more current receivers and the magnetic field can be generated with one or more magnetic field generators.

A receive electrode position module 312 can comprise CRI 306 and can be executed by the processing resource 302 to receive an electrode position signal from an electrode positioned on the medical device, the electrode position signal being generated as a result of the electrode being exposed to the electrical field. A receive magnetic position module 314 can comprise CRI 306 and can be executed by the processing resource 302 to receive a magnetic position signal from a magnetic position sensor positioned on the medical device, the magnetic position signal being generated as a result of the magnetic position sensor being exposed to the magnetic field.

A determine position module 316 can comprise CRI 306 and can be executed by the processing resource 302 to determine a magnetic position based on the magnetic position signal and an electrode position based on the electrode position signal. A determine rotation module 318 can comprise CRI 306 and can be executed by the processing resource 302 to determine a rotation of the medical device based on a shift in the electrode position with respect to the magnetic position.

Figure 10:
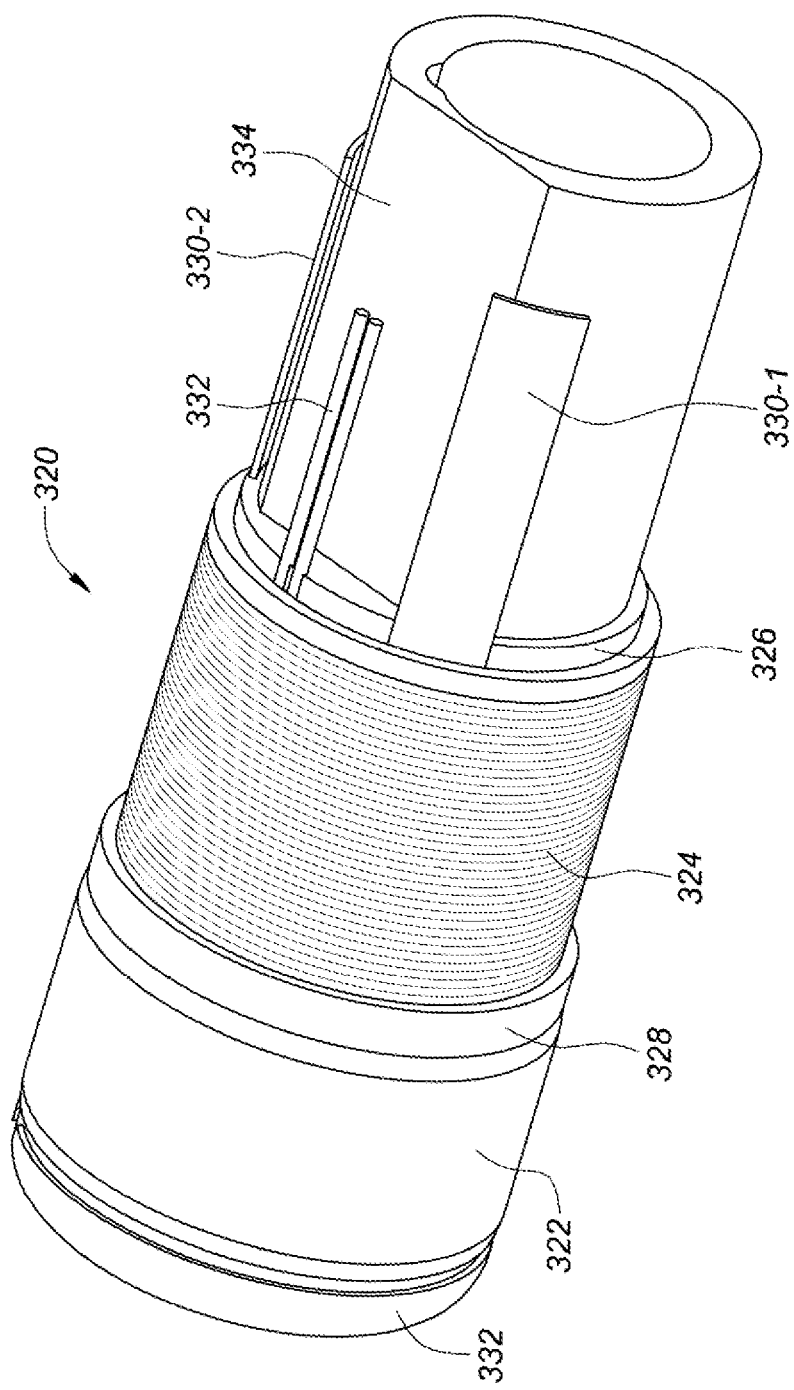
FIG. 10 is an isometric side, top, and rear view of a navigational assembly that includes a ring electrode and a magnetic position sensor, in accordance with embodiments of the present disclosure.

FIG. 10 is an isometric side, top, and rear view of a navigational assembly 320 that includes a ring electrode 322 and a magnetic position sensor 324, in accordance with embodiments of the present disclosure. In some embodiments, the navigational assembly 320 can include features similar to those navigational assemblies discussed herein. In some embodiments, the navigational assembly 320 can include a proximal end and a distal end and can extend along a longitudinal axis. The navigational assembly 320 can define a central lumen that extends along the longitudinal axis and passes through the navigational assembly 320. In some embodiments, the navigational assembly can be cylindrical in shape and can have a circular, square, triangular, etc. cross-section defined by a plane transverse to the longitudinal axis of the navigational assembly 320.

In some embodiments, the navigational assembly 320 can include a magnetic position sensor 324 disposed on the navigational assembly 320. As previously discussed, the magnetic position sensor 324 can produce a signal in response to being positioned in a magnetic field. The signal can be analyzed to determine a position and/or orientation of a medical device that includes the navigational assembly 320. As depicted, the magnetic position sensor 324 can be a coil formed by winding a filament around an elongate axis. As depicted, the magnetic position sensor 324 is wound around an outer surface of the navigational assembly 320.

In some embodiments, the navigational assembly 320 can include a magnetic position sensor positioning feature 326, as discussed in relation to FIG. 4, and can be electrically coupled to the magnetic positioning system via one or more wires 332. In an example, a proximal end of the navigational assembly can be of a first diameter and the magnetic position sensor positioning feature 326 can be of a second diameter, that is larger than the first diameter. The navigational assembly can include a distal positioning lip 328, in some embodiments. The distal positioning lip 328 can be of a greater diameter than the magnetic position sensor positioning feature 326. In some embodiments, the magnetic position sensor 324 can be wound up to the proximal side of the distal positioning lip 328.

In some embodiments, one or more field concentrating antennas 330-1, 330-2 can be disposed between the magnetic position sensor 324 and an outer surface of the navigational assembly 320, as discussed herein. For example, the one or more field concentrating antennas can be disposed between the magnetic position sensor 324 and the magnetic position sensor positioning feature 326.

In some embodiments, a ring electrode can be disposed on a distal end of the navigational assembly 320. In some embodiments, the distal positioning lip 328 can separate the magnetic position sensor 324 and the ring electrode. For example, the ring electrode 322 can abut the distal side of the distal positioning lip 328 and the magnetic position sensor can abut the proximal side of the distal positioning lip 328, as discussed herein. In some embodiments, the ring electrode 322 can be a diagnostic, therapeutic, or navigational electrode. In an example, the ring electrode 322 can be held in a fixed and precise position with respect to the magnetic position sensor 324. In some embodiments, as discussed herein, this can eliminate a calibration step associated with positioning of an electrode with respect to a magnetic position sensor.

In some embodiments, the navigational assembly 320 can include a distal cap 332, which can be connected to a distal end of the navigational assembly 320. The distal cap can be of an atraumatic design, with rounded edges. In some embodiments, the distal cap 332 can be an ablation element.

In some embodiments, the proximal portion of the navigational assembly 320 can include an alignment feature 334. In an example, the alignment feature 334 is depicted as a flat face located on the proximal portion of the navigational assembly 320. In some embodiments, the alignment feature 334 can aid in alignment between a distal end of an elongate shaft (e.g., catheter shaft) and the navigational assembly 320. Although a flat face is depicted in FIG. 9 as the alignment feature, other types of alignment features could be implemented.

Figure 11:
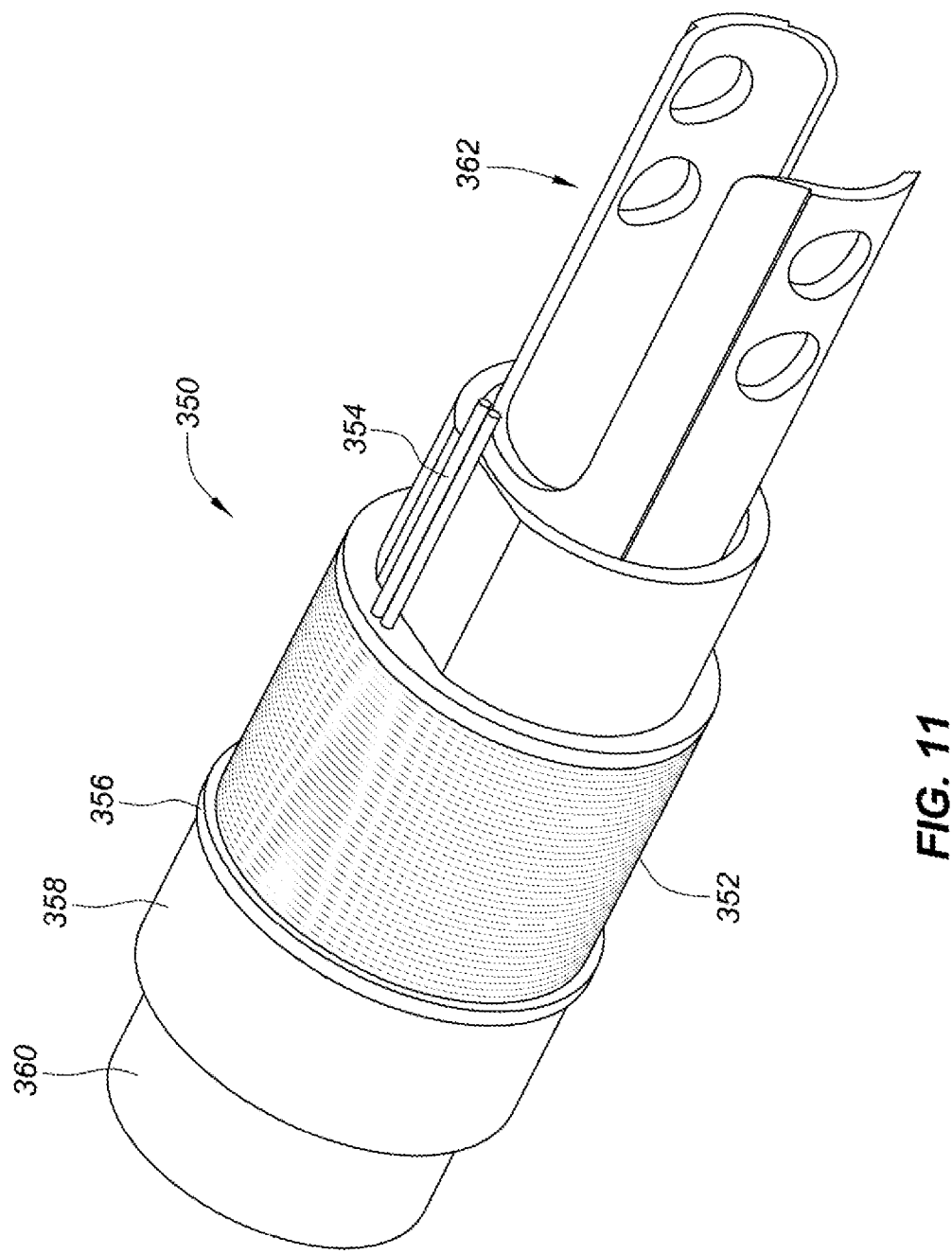
FIG. 11 is an isometric side, top, and rear view of a navigational assembly that includes a magnetic position sensor and a central mounting bore, in accordance with embodiments of the present disclosure.

FIG. 11 is an isometric side, top, and rear view of a navigational assembly 350 that includes a magnetic position sensor 352 and a central mounting bore 354, in accordance with embodiments of the present disclosure. In some embodiments, the navigational assembly 350 can include features similar to those navigational assemblies discussed herein. In some embodiments, the navigational assembly 350 can include a proximal end and a distal end and can extend along a longitudinal axis. The navigational assembly 350 can define a central lumen that extends along the longitudinal axis and passes through the navigational assembly 350. In some embodiments, the navigational assembly can be cylindrical in shape and can have a circular, square, triangular, etc. cross-section defined by a plane transverse to the longitudinal axis of the navigational assembly 350.

In some embodiments, the navigational assembly 350 can include a magnetic position sensor 352 disposed on the navigational assembly 350. As previously discussed, the magnetic position sensor 352 can produce a signal in response to being positioned in a magnetic field. The signal can be analyzed to determine a position and/or orientation of a medical device that includes the navigational assembly 350. As depicted, the magnetic position sensor 352 can be a coil formed by winding a filament around an elongate axis. As depicted, the magnetic position sensor 352 is wound around an outer surface of the navigational assembly 350.

In some embodiments, the navigational assembly 350 can include a magnetic position sensor positioning feature, as discussed previously herein, and can be electrically coupled to the magnetic positioning system via one or more wires 354. In an example, a proximal end of the navigational assembly can be of a first diameter and the magnetic position sensor positioning feature can be of a second diameter, that is larger than the first diameter. The navigational assembly 350 can include a distal positioning lip 356, in some embodiments, as discussed in relation to FIG. 10. In some embodiments, the magnetic position sensor 352 can be wound up to the proximal side of the distal positioning lip 356.

In some embodiments, a distal end of the navigational assembly 350 can include a first mounting portion 358 of a first diameter and a second mounting portion 360 of a second diameter that is less than the first diameter. The second mounting portion 360 can be disposed distally with respect to the first mounting portion 358 and about the longitudinal axis of the navigation assembly 350. Although the first mounting portion 358 and the second mounting portion 360 are depicted as cylindrical, the mounting portions 358, 360 can be of a different shape. In some embodiments, the first mounting portion 358 can be sized such that a ring electrode can be inserted onto the first mounting portion 358, similar to the ring electrode 322 discussed in relation to FIG. 10. In some embodiments, the second mounting portion 360 can be connected to a distal tip, such as a flexible tip assembly, as discussed in relation to FIG. 2.

As depicted in FIG. 11, a central mounting bore 362 can extend through a central lumen of the navigational assembly 350. In some embodiments, the central mounting bore 362 can include one or more alignment slots and/or mounting holes, as discussed in relation to FIG. 5.

Figure 12:
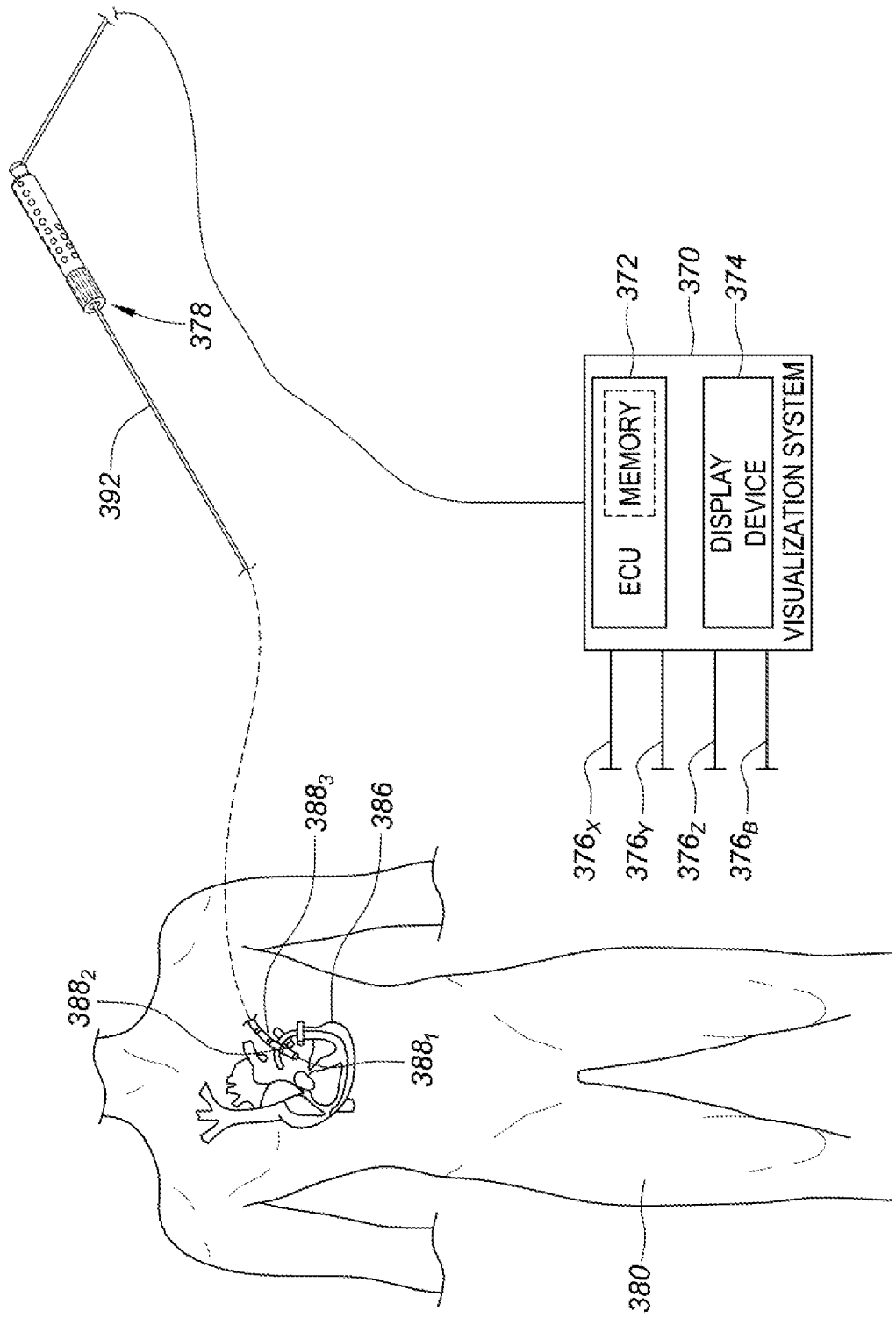
FIG. 12 is a diagrammatic view of a system, in accordance with embodiments of the present disclosure.
Figure 13:
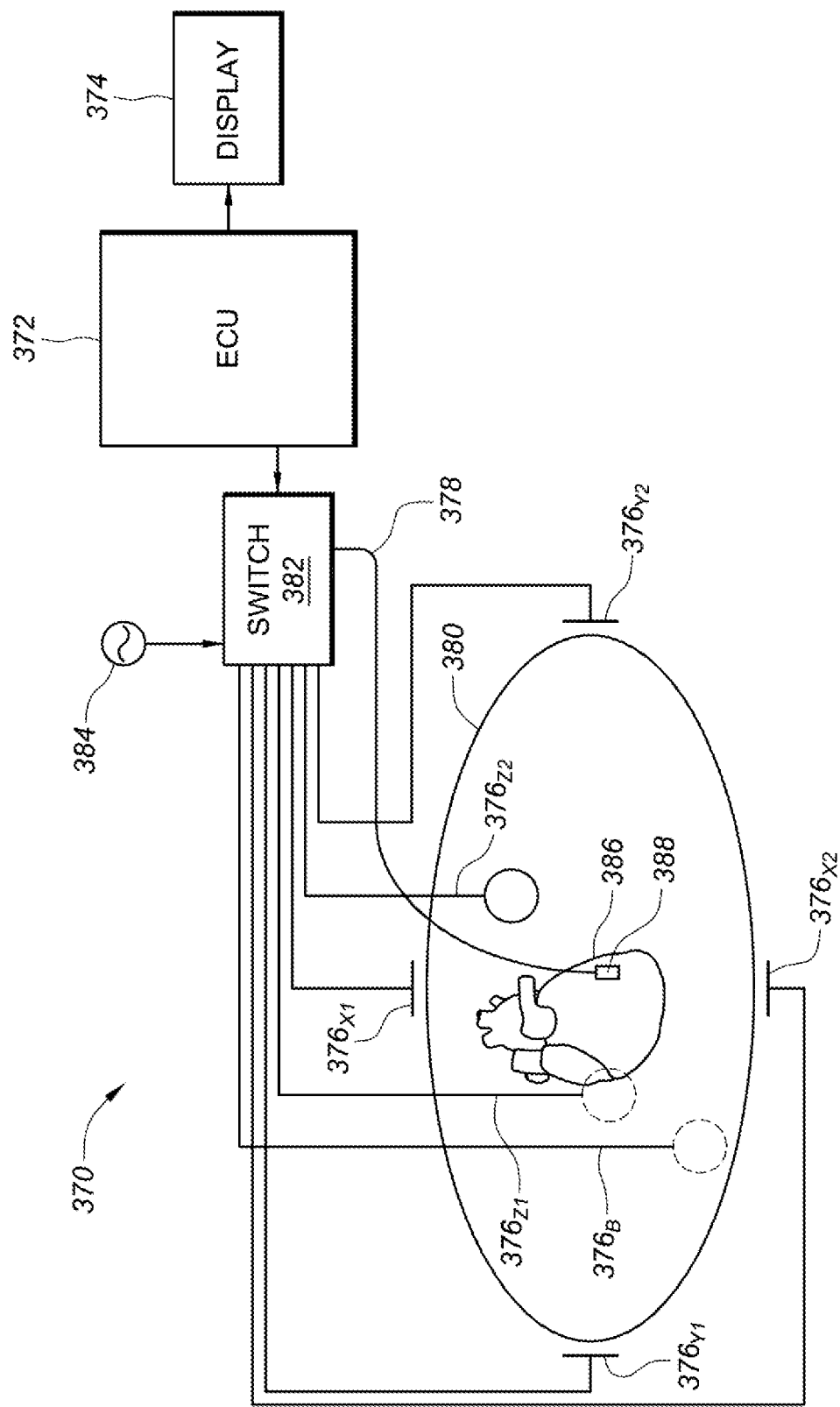
FIG. 13 is a simplified diagrammatic and schematic view of the visualization, navigation, and/or mapping system depicted in FIG. 12, in accordance with embodiments of the present disclosure.

With reference to FIGS. 12 and 13, a visualization, navigation, and/or mapping system 370 will be described. The system 370 can comprise an electric field-based system, such as, for example, the EnSite™ NavX™ system commercially available from St. Jude Medical, Inc., and as generally shown with reference to U.S. Pat. No. 7,263,397 entitled "Method and Apparatus for Catheter Navigation and Location and Mapping in the Heart," the disclosure of which is incorporated herein by reference in its entirety. In other exemplary embodiments, however, the system 370 can comprise systems other than electric field-based systems. For example, the system 370 can comprise a magnetic field-based system such as the CARTO® system commercially available from Biosense Webster, and as generally shown with reference to one or more of U.S. Pat. Nos.: 6,498,944 entitled "Intrabody Measurement;" 6,788,967 entitled "Medical Diagnosis, Treatment and Imaging Systems;" and 6,690,963 entitled "System and Method for Determining the Location and Orientation of an Invasive Medical Instrument," the disclosures of which are incorporated herein by reference in their entireties. In another exemplary embodiment, the system 370 comprises a magnetic field-based system such as the gMPS system commercially available from MediGuide Ltd., and as generally shown with reference to one or more of U.S. Pat. Nos.: 6,233,476 entitled "Medical Positioning System;" 7,197,354 entitled "System for Determining the Position and Orientation of a Catheter;" and 7,386,339 entitled "Medical Imaging and Navigation System," the disclosures of which are incorporated herein by reference in their entireties. In yet another embodiment, the system 370 can comprise a combination electric field-based and magnetic field-based system, such as, for example and without limitation, the CARTO® 3™ system also commercially available from Biosense Webster, and as generally shown with reference to U.S. Pat. No. 7,536,218 entitled "Hybrid Magnetic-Based and Impedance Based Position Sensing," the disclosure of which is incorporated herein by reference in its entirety. In yet still other exemplary embodiments, the system 370 can comprise or be used in conjunction with other commonly available systems, such as, for example and without limitation, fluoroscopic, computed tomography (CT), and magnetic resonance imaging (MRI)-based systems. For purposes of clarity and illustration only, the system 370 will be described hereinafter as comprising an electric field-based system.

As illustrated in FIGS. 12 and 13, in addition to the ECU 372 and the display 374, in an exemplary embodiment the system 370 further comprises a plurality of patch electrodes 376. With the exception of the patch electrode $376_B$ called a "belly patch," the patch electrodes 376 are provided to generate electrical signals used, for example, in determining the position and orientation of a medical device 378, and potentially in the guidance thereof. In one embodiment, the patch electrodes 376 are placed orthogonally on the surface of a patient's body 380 and used to create axes-specific electric fields within the body 380. For instance, in one exemplary embodiment, the patch electrodes $376_{x1}$, $376_{x2}$ can be placed along a first (x) axis. The patch electrodes $376_{y1}$, $376_{y2}$ can be placed along a second (y) axis. Finally, the patch electrodes $376_{z1}$, $376_{z2}$ can be placed along a third (z) axis. Each of the patch electrodes 376 can be coupled to a multiplex switch 382. In an exemplary embodiment, the ECU 372 is configured through appropriate software to provide control signals to switch 382 to thereby sequentially couple pairs of electrodes 376 to a signal generator 384. Excitation of each pair of electrodes 376 generates an electric field within the body 380 and within an area of interest such as, for example, heart tissue 386. Voltage levels at non-excited electrodes 376, which are referenced to the belly patch $376_B$, are filtered and converted, and provided to the ECU 372 for use as reference values.

As described above, the medical device 378 includes one or more electrodes 388 mounted thereon. In an exemplary embodiment, one of the electrodes 388 is a positioning electrode (however, in another exemplary embodiment, a plurality of the electrodes 388 are positioning electrodes). The positioning electrode 388 can comprise, for example and without limitation, a ring electrode or a magnetic coil sensor. The positioning electrode 388 is placed within electric fields created in the body 380 (e.g., within the heart) by exciting patch electrodes 376. The positioning electrode 388 experiences voltages that are dependent on the location between the patch electrodes 376 and the position of the positioning electrode 388 relative to the heart tissue 114. Voltage measurement comparisons made between the electrode 14 and the patch electrodes 106 can be used to determine the position of the positioning electrode 14 relative to the heart tissue 386. Movement of the positioning electrode 388 proximate the heart tissue 386 (e.g., within a heart chamber, for example) produces information regarding the geometry of the tissue 386. This information can be used, for example and without limitation, to generate models and maps of tissue or anatomical structures. Information received from the positioning electrode 388 (or if multiple positioning electrodes, the positioning electrodes 388) can be used to display on a display device, such as display device 374, the location and orientation of the positioning electrode 388 and/or the distal end of the medical device 378, and the shaft 392 thereof, in particular, relative to the tissue 386. Accordingly, among other things, the ECU 372 of the system 370 provides a means for generating display signals used to control the display device 374 and the creation of a graphical user interface (GUI) on the display device 374.

Accordingly, the ECU 372 can provide a means for determining the geometry of the tissue 386, EP characteristics of the tissue 386, and the position and orientation of the medical device 378. The ECU 372 can further provide a means for controlling various components of the system 370, including, without limitation, the switch 382. It should be noted that while in an exemplary embodiment the ECU 372 is configured to perform some or all of the functionality described above and below, in another exemplary embodiment, the ECU 372 can be a separate and distinct component from the system 370, and the system 370 can have another processor configured to perform some or all of the functionality (e.g., acquiring the position/location of the positioning electrode/sheath, for example). In such an embodiment, the processor of the system 370 would be electrically coupled to, and configured for communication with, the ECU 372. For purposes of clarity only, the description below will be limited to an embodiment wherein the ECU 372 is part of the system 370 and configured to perform all of the functionality described herein.

The ECU 372 can comprise a programmable microprocessor or microcontroller, or can comprise an application specific integrated circuit (ASIC). The ECU 372 can include a central processing unit (CPU) and an input/output (I/O) interface through which the ECU 372 can receive a plurality of input signals including, for example, signals generated by patch electrodes 376 and the positioning electrode 388, and generate a plurality of output signals including, for example, those used to control and/or provide data to the display device 374 and the switch 382. The ECU 372 can be configured to perform various functions, such as those described in greater detail below, with appropriate programming instructions or code (i.e., software). Accordingly, the ECU 372 is programmed with one or more computer programs encoded on a computer storage medium for performing the functionality described herein.

In operation, the ECU 372 generates signals to control the switch 382 to thereby selectively energize the patch electrodes 376. The ECU 372 receives position signals (location information) from the medical device 378 (and particularly the positioning electrode 388) reflecting changes in voltage levels on the positioning electrode 388 and from the non-energized patch electrodes 376. The ECU 372 uses the raw location data produced by the patch electrodes 376 and positioning electrode 388 and corrects the data to account for respiration, cardiac activity, and other artifacts using known or hereinafter developed techniques. The ECU 372 can then generate display signals to create an image or representation of the sheath medical device 378 that can be superimposed on an EP map of the tissue 386 generated or acquired by the ECU 372, or another image or model of the tissue 386 generated or acquired by the ECU 372.

In an embodiment wherein there are multiple positioning electrodes 388 (e.g., $388_1$, $388_2$, $388_3$), the ECU 372 can be configured to receive positioning signals from two or more of the positioning electrodes 388, and to then create a representation of the profile of the distal portion of the medical device 378, for example, that can be superimposed onto an EP map of the tissue 386 generated or acquired by the ECU 372, or another image or model of the tissue 386 generated or acquired by the ECU 372.

Embodiments are described herein of various apparatuses, systems, and/or methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment(s) is included in at least one embodiment. Thus, appearances of the phrases "in various embodiments," "in some embodiments," "in one embodiment," or "in an embodiment," or the like, in places throughout the specification, are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation given that such combination is not illogical or non-functional.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

Although at least one embodiment for navigational electrode with magnetic tracking coil has been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the devices. Joinder references (e.g., affixed, attached, coupled, connected, and the like) are to be construed broadly and can include intermediate members between a connection of elements and relative movement between elements. As such, joinder references do not necessarily infer that two elements are directly connected and in fixed relationship to each other. It is intended that all matter contained in the above description or shown in the accompanying drawings shall be interpreted as illustrative only and not limiting. Changes in detail or structure can be made without departing from the spirit of the disclosure as defined in the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed:

1. A medical device, comprising:
an elongate shaft extending along a shaft longitudinal axis and comprising a shaft proximal portion and a shaft distal portion;
a navigational assembly connected to the shaft distal portion and extending along the shaft longitudinal axis, the navigational assembly defining an inner lumen passing therethrough along the shaft longitudinal axis, wherein the navigational assembly includes:
a central mounting bore that includes a bore proximal end and a bore distal end, the central mounting bore extending through the inner lumen defined by the navigational assembly;
a navigational electrode positioning feature; and
a magnetic position sensor positioning feature.

2. The medical device of claim 1, wherein the navigational electrode positioning feature and the magnetic position sensor positioning feature are longitudinally spaced apart from one another.

3. The medical device of claim 2, wherein:
the navigational electrode positioning feature includes a recessed pocket in an outer surface of the navigational assembly; and
a navigational electrode is disposed in the recessed pocket.

4. The medical device of claim 3, further comprising a plurality of navigational electrode positioning features circumferentially disposed about the outer surface of the navigational assembly.

5. The medical device of claim 3, wherein:
the navigational assembly includes an electrode wire lumen extending through a wall of the navigational assembly between the recessed pocket and the inner lumen.

6. The medical device of claim 5, wherein the bore proximal end is connected to a distal end of the elongate shaft and the bore distal end is connected to a flexible tip assembly.

7. The medical device of claim 5, wherein the central mounting bore includes longitudinally extending electrode wire grooves that are aligned with the electrode wire lumens.

8. The medical device of claim 1, wherein the magnetic position sensor positioning feature includes longitudinally extending field concentrating antenna grooves formed in an outer surface thereof.

9. The medical device of claim 1, further comprising:
a plurality of navigational electrode positioning features circumferentially spaced about the navigational assembly; and
a circumferential spacing between each of the navigational electrode positioning features is equal.

10. A medical device, comprising:
an elongate shaft extending along a shaft longitudinal axis and comprising a shaft proximal end and a shaft distal end;
a central mounting bore including a bore proximal end and a bore distal end, the bore proximal end connected to the shaft distal end;
a navigational assembly defining an elongate central lumen through which the central mounting bore passes, wherein the navigational assembly includes a recessed pocket in which a navigational electrode is disposed; and
a tip assembly connected to the distal end of the central mounting bore.

11. The medical device of claim 10, wherein the navigational assembly further comprises a magnetic position sensor positioning feature, wherein the magnetic position sensor positioning feature is formed in an outer surface of the navigational assembly and includes a recessed outer surface configured for mounting a magnetic position sensor.

12. The medical device of claim 10, wherein the central mounting bore includes a central lumen extending therethrough.

13. The medical device of claim 10, wherein:
a portion of a proximal edge of the navigational assembly is longitudinally recessed; and
the central mounting bore includes a longitudinally extending electrode wire groove, wherein the longitudinally recessed proximal edge of the navigational assembly is aligned with the longitudinally extending electrode wire groove.

14. The medical device of claim 10, wherein:
the navigational assembly is formed from a non-conductive body; and
the tip assembly is a flexible tip assembly.

* * * * *